United States Patent [19]

Strausberg et al.

[11] Patent Number: 5,013,652

[45] Date of Patent: May 7, 1991

[54] COMPOSITE YEAST VECTORS

[75] Inventors: Robert L. Strausberg; Susan L. Strausberg, both of Silver Spring, Md.

[73] Assignee: Genex Corporation, Gaithersburg, Md.

[21] Appl. No.: 918,147

[22] Filed: Oct. 14, 1986

[51] Int. Cl.$^5$ ............... C12P 21/00; C12P 21/02; C12N 15/00

[52] U.S. Cl. .................... 435/69.2; 435/69.1; 435/172.3; 435/254; 435/255; 435/256; 435/320.1; 935/37; 935/56; 935/69; 935/11; 935/28; 536/27

[58] Field of Search ............ 935/28, 29, 37, 41, 935/42, 48, 56, 69; 435/68, 942, 317.1, 320, 172.3; 536/27

[56] References Cited

U.S. PATENT DOCUMENTS

| | | | |
|---|---|---|---|
| 4,517,294 | 5/1985 | Bock et al. | 435/70 |
| 4,543,329 | 9/1985 | Daum et al. | 435/69.1 |
| 4,546,082 | 10/1985 | Kurjan et al. | 435/172.3 |
| 4,661,454 | 4/1987 | Botstein et al. | 435/256 |

FOREIGN PATENT DOCUMENTS

| | | | |
|---|---|---|---|
| 0123544A2 | 10/1983 | European Pat. Off. | |
| 0100561 | 2/1984 | European Pat. Off. | |
| 0109559A1 | 5/1984 | European Pat. Off. | |
| 0109560A2 | 5/1984 | European Pat. Off. | |
| WO84/04538 | 11/1984 | European Pat. Off. | |
| 0123811A2 | 11/1984 | European Pat. Off. | |
| 0124874A2 | 11/1984 | European Pat. Off. | |
| 2128743A2 | 12/1984 | European Pat. Off. | |
| 0164556 | 12/1985 | European Pat. Off. | 435/69.1 |
| 0184575A2 | 6/1986 | European Pat. Off. | |
| 60/248181 | 12/1985 | Japan | |
| WO84/01153 | 3/1984 | PCT Int'l Appl. | |
| 84/02921 | 8/1984 | PCT Int'l Appl. | 435/172.3 |
| WO86/00923 | 2/1986 | PCT Int'l Appl. | |
| WO86/00926 | 2/1986 | PCT Int'l Appl. | |

OTHER PUBLICATIONS

Johnston, S. A. et al.; Isolation of the Yeast Regulatory Gene GAL4 and Analysis of Its Dosage Effects on the Galactose/Melibiose Regulon; Proc. Natl. Acad. Sci., 79, pp. 6971–6975, (1982).

(List continued on next page.)

*Primary Examiner*—Robin L. Teskin
*Attorney, Agent, or Firm*—Saidman, Sterne, Kessler & Goldstein

[57] ABSTRACT

A DNA sequence comprising:

(a) a hybrid first yeast promoter comprising the functional segment of the DNA sequence encoding the upstream activation site of a gene selected from the group consisting of GAL1, GAL7 and GAL10, operably linked to the functional segment of the transcription initiation site of MF-α-1;

(b) the functional segment of a signal sequence substantially comprising preferred yeast codons;

(c) the functional segment of the DNA sequence comprising a Saccharomyces GAPDH transcription terminator;

(d) the functional segment of the Saccharomyces 2μ circle replication origin; and (e) the functional segment of the yeast LEU2-d selectable marker. The DNA sequence may further comprise, inserted in phase between the signal sequence and transcription terminator, the functional segment of a DNA sequence encoding a heterologous target peptide. DNA expression vectors comprising these sequences, DNA expression systems comprising these vectors and further comprising a source of the peptide encoded by the DNA sequence of the GAL4 structural gene, yeast hosts transformed with said expression vectors or expression systems, methods of producing heterologous target peptides in yeast hosts employing the sequences, vectors and systems of the invention, and heterologous target peptides produced according to these methods are disclosed. By means of the present invention, ultrahigh (greater than 1 gram/liter, or at least 10% of total yeast cell protein) expression of heterologous peptides may be effected.

25 Claims, 36 Drawing Sheets

OTHER PUBLICATIONS

Smith, R. A. et al., Heterologous Protein Secretion from Yeast, Science, 229, pp. 1219–1224, (Sep. 1985).
Arima, K. et al., The Nucleotide Sequence of the Yeast PHO5 Gene: Aputative Precursor of Repressible Acid Phosphatase Contains a Spinal Peptide, Nucl. Acid Res., 11(6), pp. 1657–1672, (1983).
Holland, J. P. et al.; The Primary Structure of a Glycesaldehyde-3-Phosphate Dehydrogenase Gene from *S. cerevisiae*, J. Biol. Chem., 254, (19), pp. 9839–9845, (1979).
Gvarente, L. et al.; A GAL10–CYC1 Hybrid Yeast Promoter identifies the GAL4 Regulatory Region as an Upstream Site; Proc. Natl. Acad. Aci., 79, pp. 7410–7414, (1982).
Laughon et al., *Proc. Natl. Acad. Sci. U.S.A.*, 79:6827–6831, (1982).
Hinnen et al., *Chem. Ab.*, 102: Ab. No. 40931K, (1985).
Urdea et al., *Proc. Natl. Acad. Sci. U.S.A.*, 80:7461–7465, (1983).
Chen et al., *Nucleic Acids Res.*, 12:8951–8970, (1984).
Bennetzen et al., *J. Biol. Chem.*, 257:3026–3031, (1982).
Smith et al., *Science*, 229:1219–1224, (1985).
Mortimer et al., in *The Molecular Biology of the Yeast Saccharomyces: Life Cycle and Inheritance*, Strathern et al., eds., Cold Spring Harbor Laboratory, New York, pp. 11–26, (1981).
Valenzuela et al., *Nature*, 298:347–350, (1982).
Miyanohara et al., *Proc. Natl. Acad. Sci. U.S.A.*, 80:1–5, (1983).
Loison et al., *Bio/Technology*, 4:433–437, (1986).
Hitzeman et al., *Nucleic Acids Res.*, 11:2745–2763, (1983).
McAleer et al., *Nature*, 307:178–180, (1984).
Tuite et al., *Embo J.*, 1:603–608, (1982).
Mellor et al., Gene, 24:1–14, (1983).
Shimada et al., *Gene*, 39:1–9, (1985).
Giniger et al., *Cell*, 40:767–774, (1985).
Herskowitz et al., *The Molecular Biology of the Yeast Saccharomyces: Life Cycle and Inheritance*, Strathern et al., eds., Cold Spring Harbor Laboratory, N.Y., pp. 181–209, (1981).
Nasmyth, *Ann. Rev. Genet.*, 16:438–500, (1982).
Oshima, *The Molecular Biology of the Yeast Saccharomyces: Life Cycle and Inheritance*, Strathern et al., ed., Cold Spring Harbor Laboratory, N.Y., pp. 159–180, (1982).
Holland et al., *J. Biol. Chem.*, 255:2596–2605, (1980).
Holland et al., *J. Biol. Chem.*, 254:9839–9845, (1979).
Botstein et al., *The Molecular Biology of the Yeast Saccharomyces: Life Cycle and Inheritance*, Strathern et al., eds., Cold Spring Harbor Laboratory, N.Y., pp. 607–636, (1982).
Broach et al., *Gene*, 8:121–133, (1979).
Hinnen et al., *Proc. Natl. Acad. Sci. U.S.A.*, 75:1929–1933 (1978).
Beggs in *Molecular Genetics in Yeast*, VonWettstein, eds., Alfred Benzon Symposia, vol. 16, pp. 383–389, (1981).
Kurjan et al., *Cell*, 30:933–943, (1982).
Cirtron et al., *J. Bacteriol.*, 158:269–278, (1984).
Arima et al., *Nucleic Acids Res.*, 11:1657–1672, (1983).
Johnston et al., *Proc. Natl. Acad. Sci. U.S.A.*, 79:6971–6975, (1982).
Emr et al., *Proc. Natl. Sci. U.S.A.*, 80:7080–7084, (1983).
Guarante et al., *Proc. Natl. Acad. Sci. U.S.A.*, 79:7410–7414, (1982).
Technical Disclosure, 128401, (12/25/84).
Broach, *Methods Enzymol.*, 101:307–325, (1983).
Brake et al., *Proc. Natl. Acad. Sci. U.S.A.*, 81:4642–4646, (1984).
Filho et al., *Biotechnology*, 4:311–315, (1986).
Julius et al., *Cell*, 37:1075–1089, (1984).
Wood et al., *Nature*, 314:446–449, (1985).

Construction of At-III
Expression Vector YpGX228

Construction of Expression Vector YpGX229

Construction of M13 Vector MGX69

Construction of Expression Vector YpGX235

Organization of the GAL1 and GAL10 Genes in
*Saccharomyces cerevisiae*

Addition of HindIII and XhoI Sites to the GAL 1-10 Regulatory Region

*oligonucleotide-directed mutagenesis

Restriction Sites in the GAL 1-10
Regulatory Region Created by
Oligonucleotide-Directed Mutagenesis Addition of a Xhol Site to the α-Factor Regulatory Region

Assembly of a Yeast-E. coli Shuttle Vector Including the α-Factor Prepro-Lys-Arg-At-III Gene Insertion of the GAL UAS Adjacent to the α-Factor Prepro-Lys-Arg-At-III Gene Insertion of the GAL4 Gene into YpGX243

Galactose-Regulated Expression of At-III

Deletion of α-Factor Pro-Lys-Arg and Addition of a Xhol Site to the α-Factor Regulatory Region

Assembly of an Expression Vector Including the α-Factor Pre-At-III Gene

Assembly of a Yeast E. coli Shuttle Vector Including the α-Factor Pre-At-III Gene

Assembly of a Galactose-Regulated α-Factor Pre-At-III Gene

Addition of the GAL4 Gene to YpGX246

Deletion of the α-Factor Pre Sequence and the Addition of a Xhol Site to the α-Factor Regulatory Region Assembly of a Gene Encoding PHO5 Signal-At-III

Assembly of a Yeast-E. coli Shuttle Vector Including the PHO5 Signal-At-III Gene Assembly of a Galactose-Regulated
PHO5 Signal-At-III Gene Addition of the GAL4 Gene to YpGX262

Assembly of a Gene Encoding
SUC2 Signal-At-III

Assembly of a Yeast-E. coli Shuttle Vector Including the SUC2 Signal-At-III Gene

Assembly of a Galactose-Regulated
SUC2 Signal-At-III Gene

Addition of the GAL4 Gene to YpGX254

Assembly of a Gene Encoding Pre-At-III

Assembly of a Yeast-E. coli Shuttle Vector
Including the Pre-At-III Gene**

Assembly of a Galactose-Regulated
Pre-At-III Gene

Addition of the GAL4 Gene to YpGX264

Detection of PHO5 Signal-At-III Protein by
Coomassie Staining of an SDS-Polyacrylamide Gel

Figure 33

```
                                                                                              -170
                                                                                              AGTG
     -160       -150       -140       -130       -120       -110       -100        -90
CAAGAAAACCAAAAAGCAACAACAGGTTTTGGATAAGTACATATATATAGAGGGCCCTTTGTTCCCATCAAAAATGTACTGTT

-80        -70        -60        -50        -40        -30        -20        -10
CTTACGATTCATTTACGATTCAAGAATAGTTCAAACAAGAAGATTACAAACTATCAATTCATACACATATAAACGACCAAA 1         10              20   PstI       30               40              50          60
AGA ATG AGA TTT CCT TCA ATT TTT ACT GCA GTT TTA TTC GCA GCA TCC TCC GCA TTA GCT GCT
    met arg phe pro ser ile phe thr ala val leu phe ala ala ser ser ala leu ala ala
    1                                      10                                      20

70               80              90              100            110          120
CCA GTC AAC ACT ACA GAT GAA ACG GCA CAA ATT CCG GCT GTC GAA GCT GTC ATC GGT TAC
pro val ASN THR THR thr glu asp glu thr ala gln ile pro ala glu ala val ile gly tyr
                    30                                      40

130            140             150            160            170         180
TCA GAT TTA GAA GGG GAT TTC GAT GTT GCT GTT TTG CCA TTT TCC AAC AGC ACA AAT AAC GGG
ser asp leu glu gly asp phe asp val ala val leu pro phe ser ASN SER THR asn asn gly
                    50                                      60

190           200              210            220            230            240
TTA TTG TTT ATA AAT ACT ACT AAT GCC AGC ATT GCT AAA GCT AAA GAA GGG GTA TCT TTG GAT
leu leu phe ile ASN THR THR ile ala ser ile ala lys ala lys glu gly val ser leu asp
              70                                      80

250           260    HindIII 270                280              290            300
AAA AGA GAG           GCT GAA GCT TGG CAT TGG TTG CAA CTA AAA CCT GGC CAA CCA ATG TAC
lys arg glu           ala glu ala trp his trp leu gln leu lys pro gly gln pro met tyr
*********             *********                                                    102
                                90

310           320   HindIII              340            350            360
AAG AGA GAA GCC GAA GCT TGG CAT TGG CTG CAA CTA AAG CCT GGC CAA CCA ATG TAC
lys arg glu ala glu ala trp his trp leu gln leu lys pro gly gln pro met tyr
*********             *********                                             123
                                111
```

Figure 33 (Continued)

```
370       380            HindIII     400         410         420         430
AAA AGA GAA GCC GAC GCT GAA GCT TGG CAT TGG CTG CAA CTA AAG CCT GGC CAA CCA ATG TAC
lys arg glu ala asp ala glu ala trp his trp leu gln leu lys pro gly gln pro met tyr
***************************                                                    144
                                                                               132
        440         450   HindIII     470         480         490
AAA AGA GAA GCC GAC GCT GAA GCT TGG CAT TGG TTG CAG TTA AAA CCC GGC CAA CCA ATG TAC
lys arg glu ala asp ala glu ala trp his trp leu gln leu lys pro gly gln pro met tyr
***************************                                                    165
                                                                               153
500         510         520         530  SalI 540         550         560         570
TAA GCCCGACTGATAACAACAGTGTAGATGTAACAAAGTCGACTTTGTTCCCACTGTACTTTTAGCTCGTACAAATACAAT
stop
580         590         600         610         620         630         640         650         660
ATACTTTCATTTCTCCGTAAACAACCTGTTTTCCCATGTAATATCCTTTTCTATTTTCGTTTCGTTACCAACTTTACACAT
670
ACTTTATATAGCTAT
```

COMPOSITE YEAST VECTORS

BACKGROUND OF THE INVENTION

Field of the Invention

The present invention relates to a method of expressing genes in yeast. More particularly, the invention relates to a method of expressing foreign genes in yeast. The invention further relates to composite DNA expression vectors capable of effecting ultrahigh expression of a polypeptide in a yeast host, yeast cells transformed by the DNA expression vector, use of the DNA expression vector to effect ultrahigh expression of a target polypeptide, and to target polypeptide products produced by yeast cells transformed by the DNA expression vectors.

Background of the Invention

The culture of various yeast strains has long been of great practical and economic importance. A description of commonly used yeasts and their characteristics may be found in *Reminqton's Pharmaceutical Sciences*, 16th Edition, A. Osol, ed., Mack Publishing Co., Easton, Penn., pp. 1276-1277 (1980). Large scale culture of this eukaryotic organism on an industrial scale is well known, Burrow, "Baker's yeast," p. 349-420, in, *The Yeast*, vol. 3, Rose and Harrison, eds., Academic Press, London (1970), and it has been suggested that existing know-how and technologies of large scale yeast culture might be advantageously adapted to the production of polypeptides. Loison et al., Bio/Technology 4:433-437 (1986). In addition, the use of yeasts such as Saccharomyces as hosts for expressing mammalian and other foreign proteins offers advantages lacking in more commonly used prokaryotic hosts such as *Escherichia coli*. For example, yeasts are capable of glycosylation while prokaryotic hosts such as *E. coli* are not. *S. cerevisiae* is generally regarded as safe by the United States Food and Drug Administration. The genetic system of *S. cerevisiae* has been well-defined. See, e.q., Mortimer et al., "Genetic Mapping in *Saccharomyces cerevisiae*," in, The Molecular Biology of the Yeast Saccharomyces: Life Cycle and Inheritance, Strathern et al., eds., Cold Spring Harbor Laboratory, N.Y., pp. 11-26 (1981). The principles controlling gene expression in *S. cerevisiae* are also well characterized. *See generally,* Strathern et al., eds., The Molecular Biology of the Yeast Saccharomyces: Metabolism and Gene Expression, Cold Spring Harbor Laboratory, N.Y. (1982). Saccharomyces has thus recently been used to express such foreign polypeptides as hepatitis B, Valenzuela et al., Nature 298:347-350 (1982); Miyanohara et al., Proc. Natl. Acad. Sci. USA 80:1-5 (1983); Hitzeman et al., Nucleic Acids Res. 11:2745-2763 (1983); McAleer et al., Nature 307:178-180 (1984), interferons, Tuite et al., EMBO J. 1:603-608 (1982), calf chymosin, Mellor et al., Gene 24:1-14 (1983), epidermal growth factor, Urdea et al., Proc. Natl. Acad. Sci. USA 80:7461-7465 (1983), and calf prochymosin, Smith et al., Science 229:1219-1224 (1985).

In spite of the advantages of using a yeast such as Saccharomyces as an expression host, production of heterologous polypeptides generally has been disappointingly low as compared to that of the normal homologous gene products. Chen et al., Nucleic Acids Res. 12:8951-8970 (1984). Many investigators have sought to increase expression of proteins, especially of heterologous proteins, in yeast hosts by employing in an expression vector various components and combinations thereof that might be expected to increase heterologous protein expression because they are thought to strongly express homologous gene products in yeasts. Generally, these expression vectors have included a strong yeast promoter to direct transcription, a yeast sequence to terminate transcription, and a replication origin and selectable marker to maintain the plasmid in the host cell. The promoter and terminator sequences have generally been chosen from highly expressed yeast genes. Promoter sequences often have been selected based on their ability to tightly regulate expression of the foreign product which sometimes is toxic to the host cell.

For example, European Patent Application No. 84303833.2 (Pub. No. 0 128 743 A2) discloses a cloning vector containing a foreign gene and the yeast galactokinase (GAL1) regulatory region and promoter in position to regulate the expression of the foreign gene. This system was used to produce a galactokinase-bovine prochymosin fusion protein in *S. cerevisiae*. Also disclosed is the use of increased copy number for the GAL4 gene, known to enhance messenger RNA levels of the galactose metabolic genes in yeast, (Laughon et al., Proc. Natl. Acad. Sci. USA 79:6827-6831 (1982)), by isolating the GAL4 gene from yeast DNA and inserting it into a plasmid which contains the GAL1 regulatory region and promoter as well as the foreign gene.

European Patent Application No. 84101937.5 (Pub. No. 0 123 811 A2) discloses use of a GAL1 promoter of the yeast galactokinase gene in expressing a desired protein. The GAL1 promoter used was a DNA segment containing the transcription start signal for galactokinase in *S. cerevisiae*.

European Patent Application No. 84302723.6 (Pub. No. 0 123 544 A2) discloses use of the promoter and signal peptide portions of the yeast alpha-factor gene joined to the sequence encoding the desired heterologous protein. This system was used to express human interferon gamma, human serum albumin, bovine interferon alpha-1 and alpha-2, tissue plasminogen activator, rennin and a human insulin-like growth factor.

PCT Application No. WO 86/00926 discloses use of controllable repressor operator sequences responsive to the a 1/alpha-2 and alpha-2 gene products of the type a and type alpha yeast mating locus alleles to repress expression of a heterologous structural gene located downstream of the expression controlled sequence in the presence of a gene product of a yeast mating type locus.

PCT Application No. *83/01370* (Pub. No. WO *84/01153*) discloses use of the SUC2 promoter, containing the transcription start signal for the structural gene for invertase to direct expression of an interferon gene within a yeast cell. The system allows passive regulation of interferon production, and was used to express human leukocyte interferon in *S. cerevisiae*.

European Patent Application No. *84104967.9* (Pub. No. 0 124 874 A2) discloses use of the 5'-flanking region from the yeast repressible acid phosphatase (PHO5) gene to tightly regulate the expression of heterologous genes in yeast. The PHO5 promoter/regulator was used to direct expression of interferon in *S. cerevisiae*.

European Patent Application No. *83110472.4* (Pub. No. 0 109 560 A2) discloses use of the promoter of the PHO5 gene, including the PHO5 signal peptide, to control expression of a target peptide gene in *S. cerevisiae*. The system was used to express norepinephrine alpha. Production of the target protein varied as a function of the phosphate concentration in the medium.

PCT Application No. 85/01470 (Pub. No. WO 86/00923) discloses use of a PHO5 promoter lying within the approximately 0.55 Kb sequence preceding the ATG translational start triplet at the beginning of the PHO5 coding sequence, which is excised and isolated from the PHO5 gene, to control expression of a heterologous peptide in S. cerevisiae. This PHO5 promoter system, in one embodiment containing also the major PHO5 start site, is used to direct expression of human fertility hormones, such as hCG, LH and FSH. Also disclosed is use of the promoter sequence of the gene encoding yeast glyceraldehyde-3'-phosphate alhydrogenase (GAPD) to control heterologous protein expression.

Hinnen et al., Chem. Ab. 102:Ab. No. 40931k (1985) discloses use of the promoter and 80% of the 5' end of the PHO5 signal sequence fused to a cDNA fragment encoding the mature protein sequence and a portion of the 3' end of the signal sequence of human alpha interferon. This system thus includes a hybrid PHO5-hIF-alpha signal sequence used to transform S. cerevisiae.

European Patent Application No. 83310471.6 (Pub. No. 0 109 559 A1) discloses use of the glyceraldehyde-3-phosphate dehydrogenase promoter to control expression of a target peptide in Saccharomyces. Also disclosed is the use of the 3'-terminal non-translational region of the GAPDH gene in the plasmid at a point downstream from the target peptide gene to increase production of the target peptide.

PCT Application No. 84/00153 (Pub. No. WO 84/04538) discloses use of a yeast regulon and a transcription terminator derived from one of the GAPDH genes of S. cerevisiae. It is disclosed that a 850 nucleotide GAPDH regulon was almost 100 times more effective as smaller regulons (280 nucleotides). Also disclosed is the use of the GAPDH regulon in conjunction with a signal sequence derived from a gene for yeast invertase, yeast acid phosphatase, unmatured forms of thaumatin-like proteins, unmatured forms of chymosin-like proteins or two consensus signal polypeptides, the amino acid sequences of which are disclosed. Also disclosed is the use of preferred yeast codons in either the target peptide sequence, the signal sequence or both.

Urdea et al., Proc. Natl. Acad. Sci. USA 80:7461-7465 (1983) discloses a plasmid containing the yeast GAPDH promoter, the structural gene for human epidermal growth factor (urogastrone) and a terminator derived from yeast alcohol dehydrogenase (ADH). This genetic unit was inserted into a yeast plasmid vector that contained the yeast 2 micron sequences, a DNA fragment containing the yeast LEU coding sequences, and a fragment of pBR322 containing the origin of replication and the ampicillin resistance gene, and used to direct synthesis of urogastrone. The DNA sequence for the gene encoding urogastrone was designed with yeast-preferred codons inferred from codon usage in the highly expressed yeast genes for GAPDH, ADH and pyruvate kinase. This expression system produced about 30 micrograms of target protein per liter of yeast culture.

European Patent Application No. 85870170.9 (Pub. No. 0 184 575 A2) discloses the use of strong yeast promoters such as the promoters of alcohol dehydrogenase (ADH1), enolase (EN08; ENO46), glyceraldehyde-3-phosphate dehydrogenase (GAP63; GAP491), phosphoglycerate kinase (PGK), alkaline phosphatase (PHO3; PHO5) and promoter p415, to control expression of enzymes of the 1,4-beta-N-acetylmuramidase type.

Bock et al., U.S. Pat. No. 4,517,294, disclose that a plasmid vector containing four components is required to express a heterologous gene such as the cDNA for human antithrombin III in yeast. The first component allows for transformation of both E. coli and yeast, and contains a selectable gene from each organism. The second component is a 5'-flanking sequence from a highly expressed yeast gene to promote transcription of a downstream-placed structural gene, such as the 5'-flanking sequence from yeast 3-phosphoglycerate kinase (PGK). The third component is a structural gene containing both an ATG translation start and translation stop signals. The fourth component is the 3'-flanking sequence of a yeast gene containing the signal for transcription termination and polyadenylation. Bock et al. further describe plasmids directing the production of antithrombin III in yeast.

In spite of these advances in the development of yeast vectors, expression of heterologous gene products has been much reduced compared with expression of homologous proteins in the same expression vector. Thus, Chen et al., Nucleic Acids Res. 12(23):8951-8970 (1984) noted that accounts of expression experiments involving interferons, hepatitis surface antigen, chymosin and human growth hormone reported heterologous protein levels far below the levels of normal homologous yeast gene products. This phenomenon, which is not well understood, often reduces the expression of the foreign gene product to milligrams or even micrograms per liter of cell culture. Such low production limits the utility of yeast as a host for heterologous protein expression. Chen et al. used the promoter sequence and transcription termination and polyadenylation sequence from the 3-phosphoglycerate kinase (PGK) gene to control expression of interferon in yeast, and reported expression 15-50 times lower than expression of the natural homologous PGK gene on the same plasmid. Chen et al. found that the difference was directly proportional to changes in steady-state levels of mRNAs, but could not explain the relationship.

Another suggested explanation for the relatively poor expression of heterologous genes in yeast has been that the codons used to direct protein synthesis in mammalian genes differ significantly from those used for highly expressed homologous yeast genes. It is well known that, because the genetic code is degenerate, several different codons can specify the inclusion of a given amino acid in a growing polypeptide chain. Nirenberg et al., "The RNA Code and Protein Synthesis," in, L. Frisch, ed., Symposia on Quantitative Biology XXXI, Cold Spring Harbor Laboratory, Publisher, N.Y. pp. 11-24 (1966). The highly expressed yeast genes contain a high proportion of specific codons which correspond to prominent tRNA species present in the cell. Genes which are expressed less efficiently generally include a more random codon choice for a particular amino acid. Bennetzen et al., J. Biol. Chem. 257:3026-3031 (1982). Since mammalian and other genes generally do not utilize these so-called "preferred" yeast codons, this might explain the observed limited expression. Urdea et al., supra, discussed above, used such an approach and reported enhanced expression of urogastrone under the control of a GAPDH promoter and ADH terminator in yeast. However, heterologous protein expression was low (about 30 micrograms/liter of culture) in comparison with expected homologous gene production.

In further refining yeast expression vectors to optimize production of foreign gene products, expression elements from different yeast genes have been combined to create hybrid expression vectors, such as those described hereinabove. Observed improvement in heterologous expression, however, generally has not been dramatic. For example, Smith *et al., Science* 229:1219-1224 (1985) employed many different combinations of promoter and secretion-signal sequences to control expression of prochymosin in yeast. Examination of total antigen production (see, Table 1 of Smith et al.) shows very little difference in prochymosin production among the various combinations employed, including a GAL1-PHO5 combination.

Thus, in spite of recent advances in yeast vector technology, a need has continued to exist for a DNA expression vector capable of effecting expression of heterologous polypeptides in yeast hosts at high expression levels.

SUMMARY OF THE INVENTION

Recognizing the need for the development of a yeast DNA expression vector capable of highly efficient expression of heterologous polypeptides in yeast hosts, the present inventors have developed an expression vector capable of directing heterologous polypeptide expression at high expression levels for yeast hosts. In fact, the present invention provides for expression of many heterologous polypeptides in yeast hosts at minimum levels of one gram per liter of yeast culture, or at least 10% of total yeast cell protein. Accordingly, the present invention provides a means of expressing heterologous peptides in yeast at a level which is termed "ultrahigh" for the purposes of describing the invention herein. Thus, according to the present invention, there is provided a combination of yeast expression elements comprising a vector capable of effecting ultrahigh expression of a heterologous polypeptide in a yeast host. The ultrahigh expression obtained according to the present invention is surprisingly greater than that which would be expected based upon the known effects of the individual elements themselves.

In one embodiment of the present invention, there is provided a DNA expression system comprising:
 (I) a DNA expression vector capable of effecting expression of a polypeptide in a yeast host comprising, in phase:
  (a) a hybrid first yeast promoter comprising the functional segment of the regulatory region of a galactose-inducible promoter gene operably linked to the functional segment of the transcription initiation site of a highly expressed yeast gene;
  (b) the functional segment of a signal sequence, said signal sequence substantially comprising preferred yeast codons;
  (c) the functional segment of a DNA sequence encoding a transcription terminator;
  (d) a yeast replicon;
  (e) the functional segment of a DNA sequence encoding a selectable yeast marker; and
 (II) a source of the peptide encoded by the DNA sequence of the GAL4 structural gene.

The DNA expression system of the present invention is useful for expressing many different heterologous polypeptides. Thus, in another embodiment, the invention provides for a DNA expression system as described above, further comprising, inserted in phase between the signal sequence and the transcription terminator, the functional segment of a DNA sequence encoding a heterologous target polypeptide. In another embodiment, the invention provides for yeast hosts transformed with the DNA expression vector of the DNA expression system as described above. In another embodiment, the invention provides for a method of producing a heterologous target polypeptide in a yeast host, comprising culturing said yeast host transformed with a DNA expression vector of the DNA expression system as described above, causing expression of said target polypeptide, and recovering said target polypeptide.

In another embodiment of the invention, the DNA expression vector of the DNA expression system described above may be in the form of a plasmid. Alternatively, the DNA sequence comprising the DNA expression vector of the DNA expression system described above may be integrated into yeast chromosomal material.

| Strain Number | Strain Designation |
|---|---|
| 1 | G20 |
| 2 | G20(YpGX243) |
| 3 | G20(YpBX243GAL4) |
| 4 | 422(YpGX243 + pSJ3) transformant #1 |
| 5 | 422(YpGX243GAL4) transformant #1 |
| 6 | 422(YpGX243GAL4) transformant #2 |
| 7 | 422(YpGX243GAL4) transformant #3 |
| 8 | 422(YpGX243GAL4) transformant #4 |
| 9 | 422(YpGX243 + pSJ3) transformant #2 |

-continued

| Strain Number | Strain Designation |
|---|---|
| 10 | D5(YpGX243GAL4) transformant #1 |
| 11 | D5(YpGX243GAL4) transformant #2 |
| 12 | D5(YpGX243GAL4) transformant #3 |
| 13 | D5(YpGX243GAL4) transformant #4 |

Figure 13:
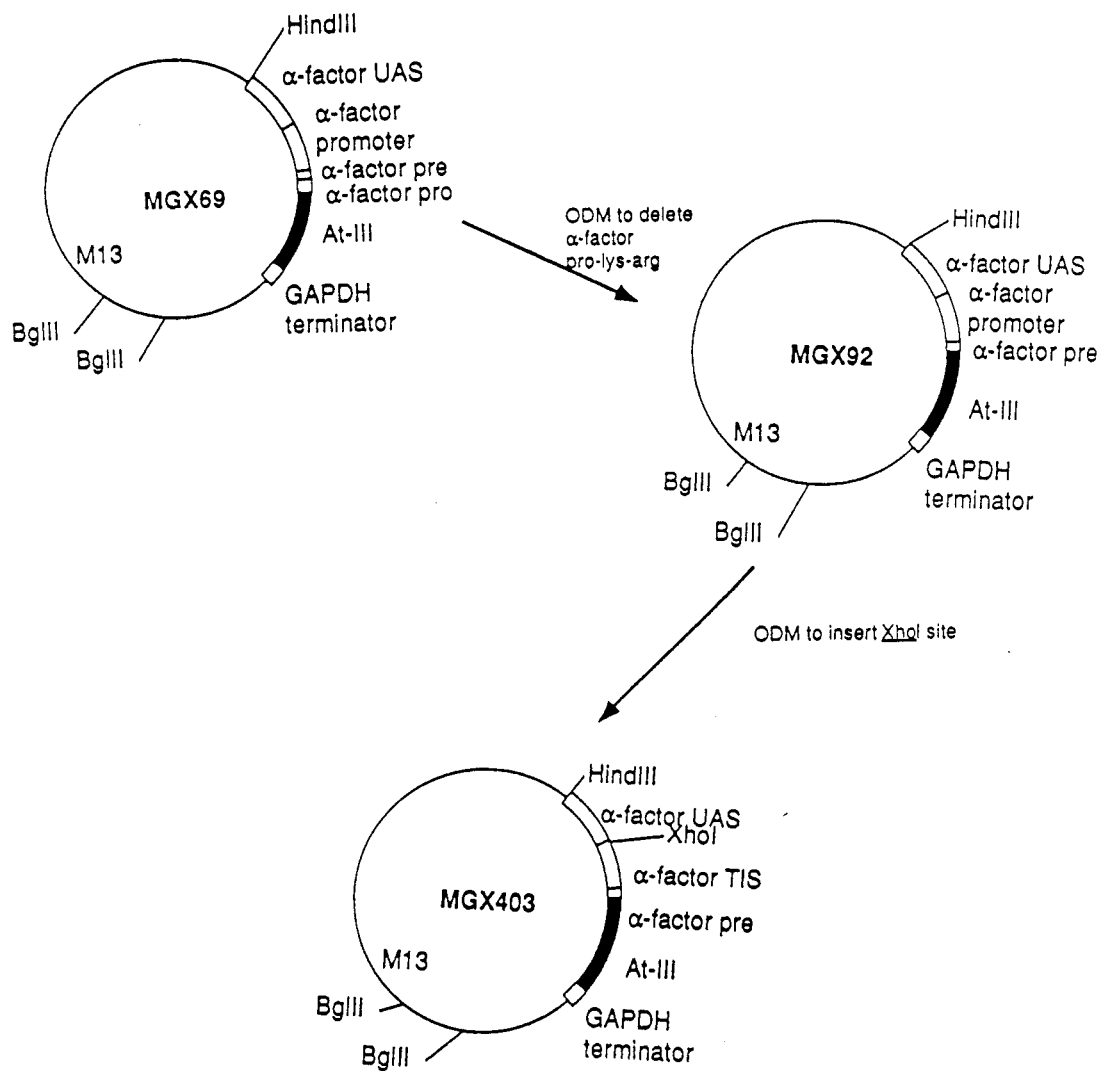

FIG. 13 is a flow chart showing the deletion of alpha-factor Pro-Lys-Arg and addition of a XhoI site to the alpha-factor regulatory region.

Figure 14:
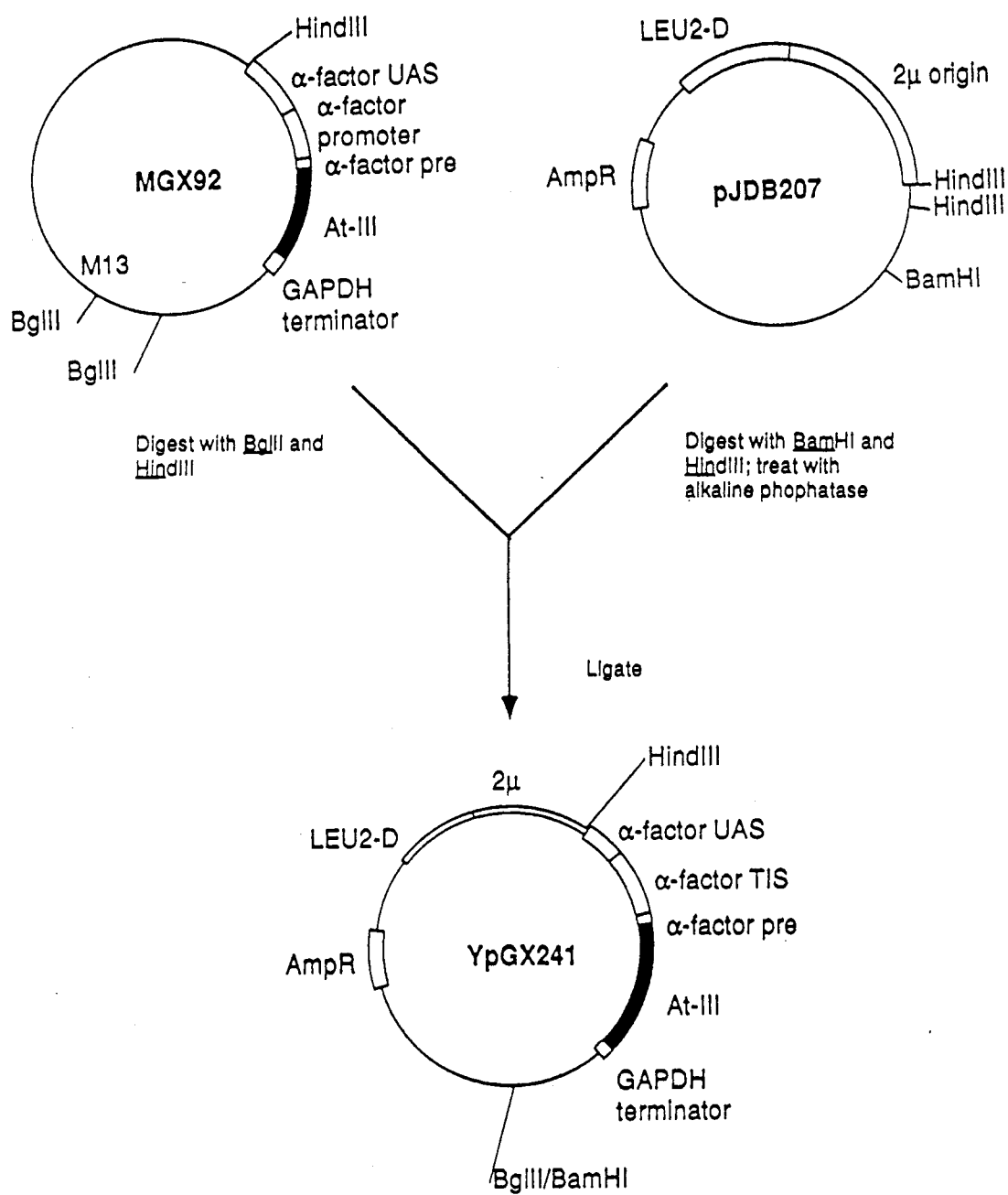

FIG. 14 is a flow chart showing the assembly of an expression vector including the alpha-factor Pre-At-III gene.

Figure 15:
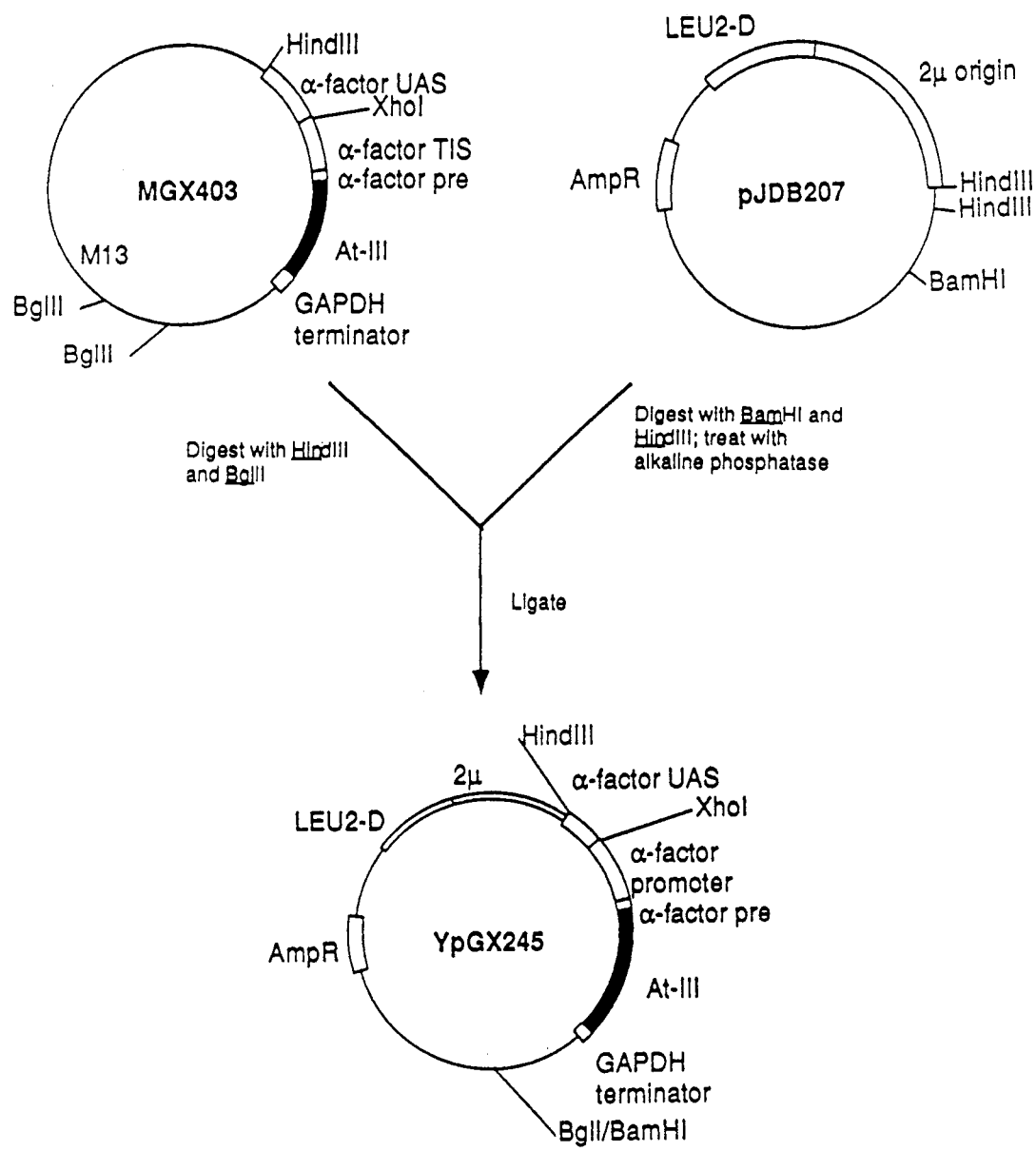

FIG. 15 is a flow chart showing the assembly of a yeast-E. coli shuttle vector including the alpha-factor Pre-At-III gene.

Figure 16:
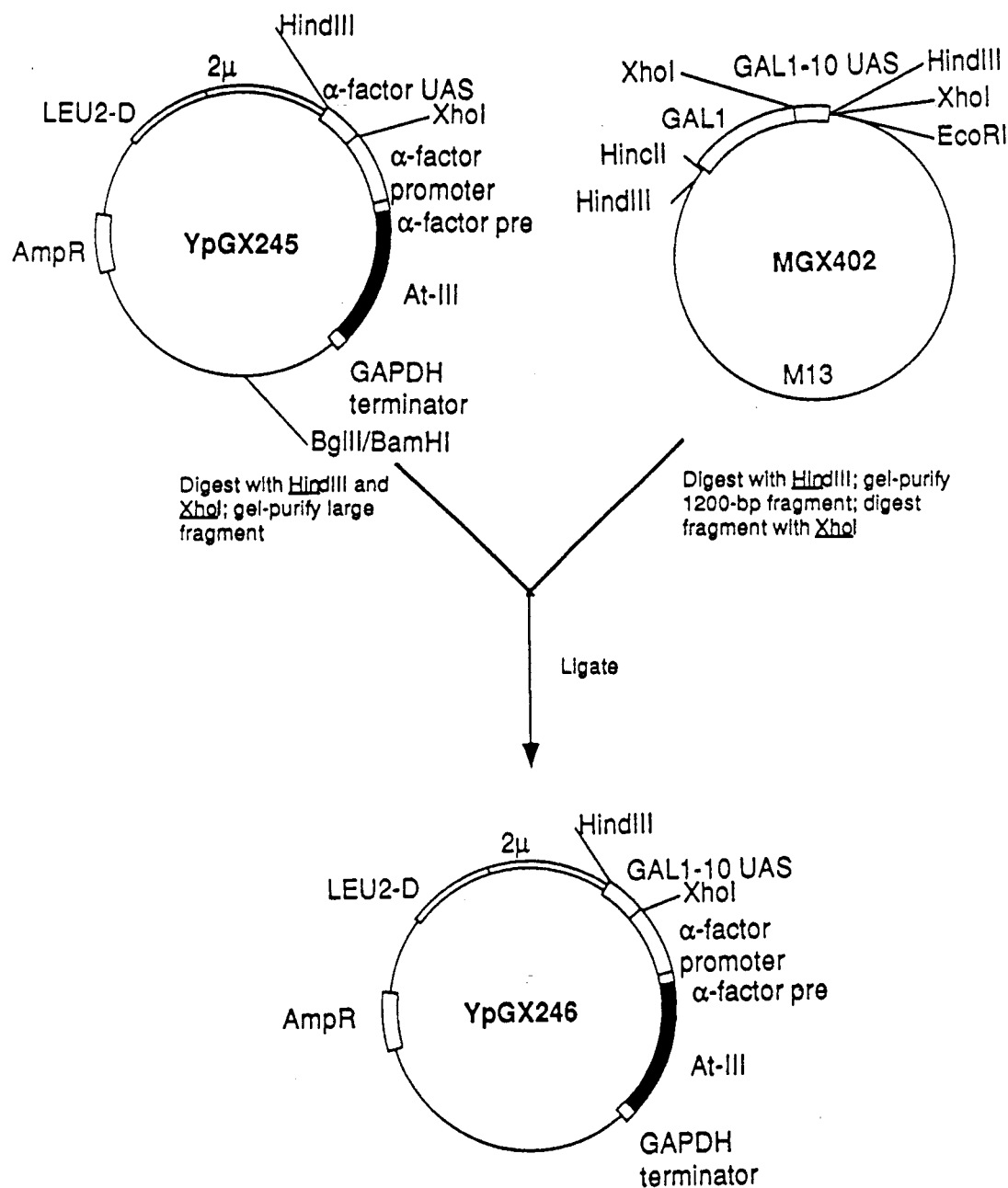

FIG. 16 is a flow chart showing the assembly of a galactose-regulated alpha-factor Pre-At-III gene.

Figure 17:
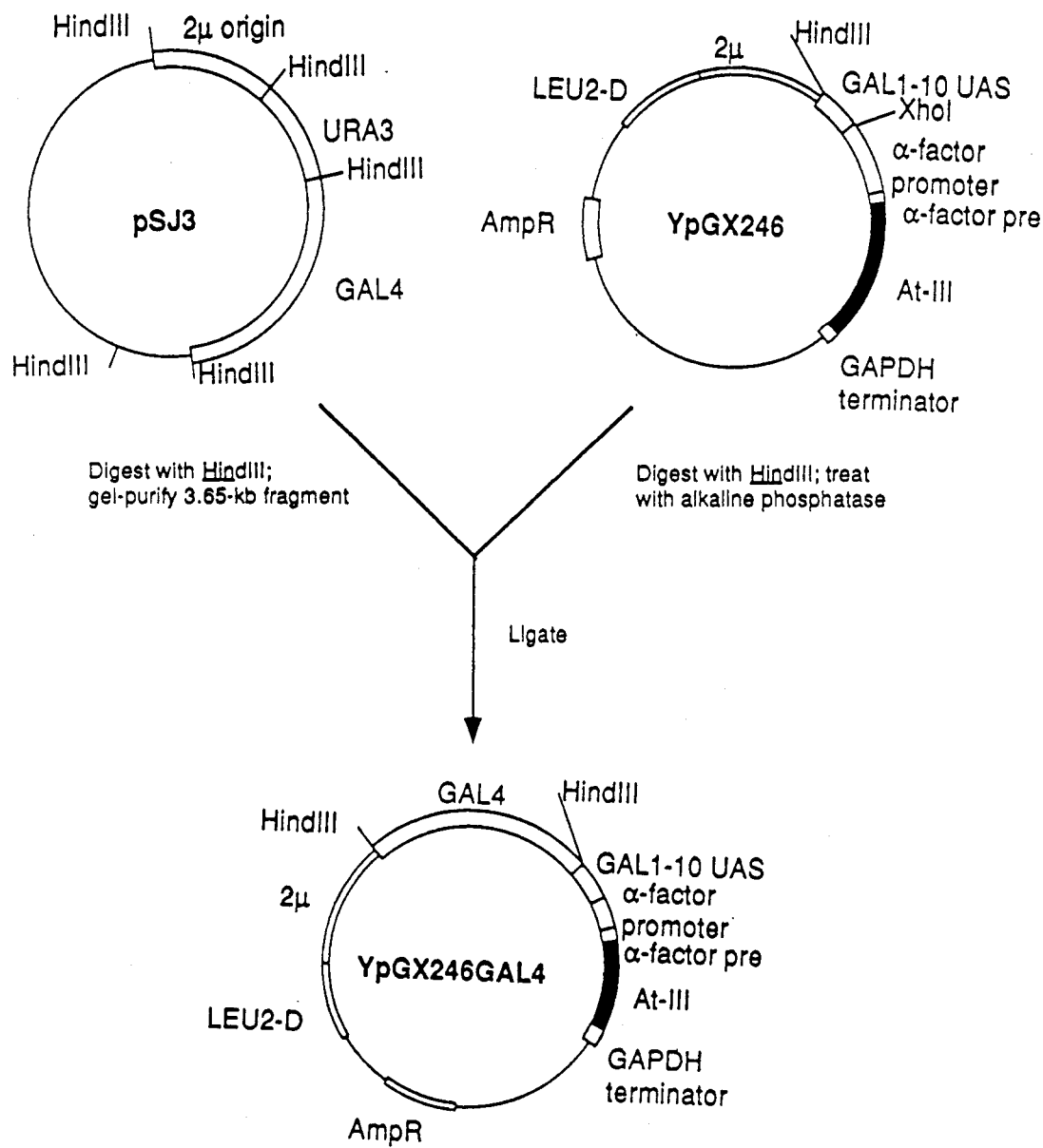

FIG. 17 is a flow chart showing the addition of the GAL4 gene to the plasmid YpGX246.

Figure 18:
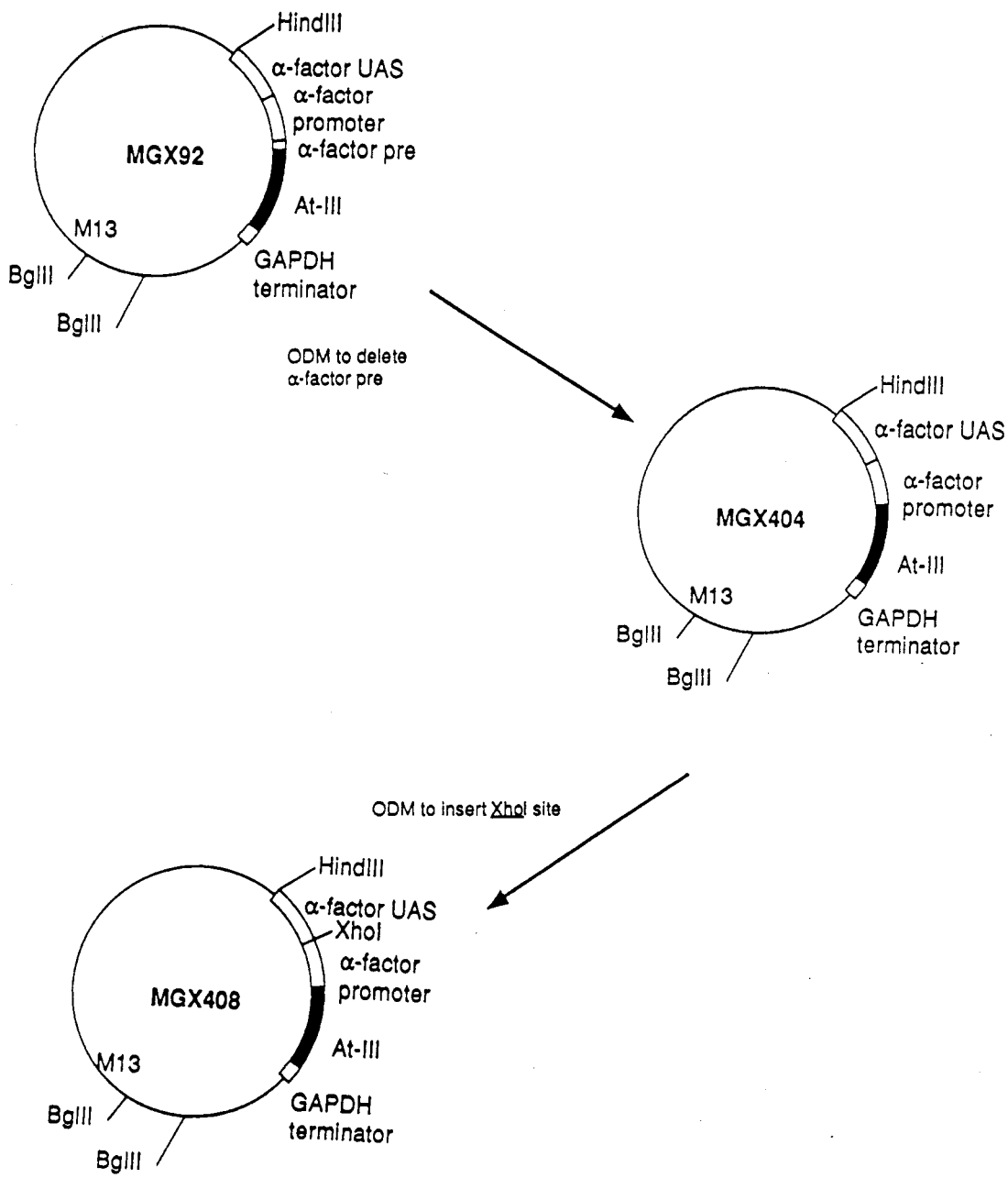

FIG. 18 is a flow chart showing the deletion of the alpha-factor Pre sequence and the addition of a XhoI site to the alpha-factor regulatory region.

Figure 19:
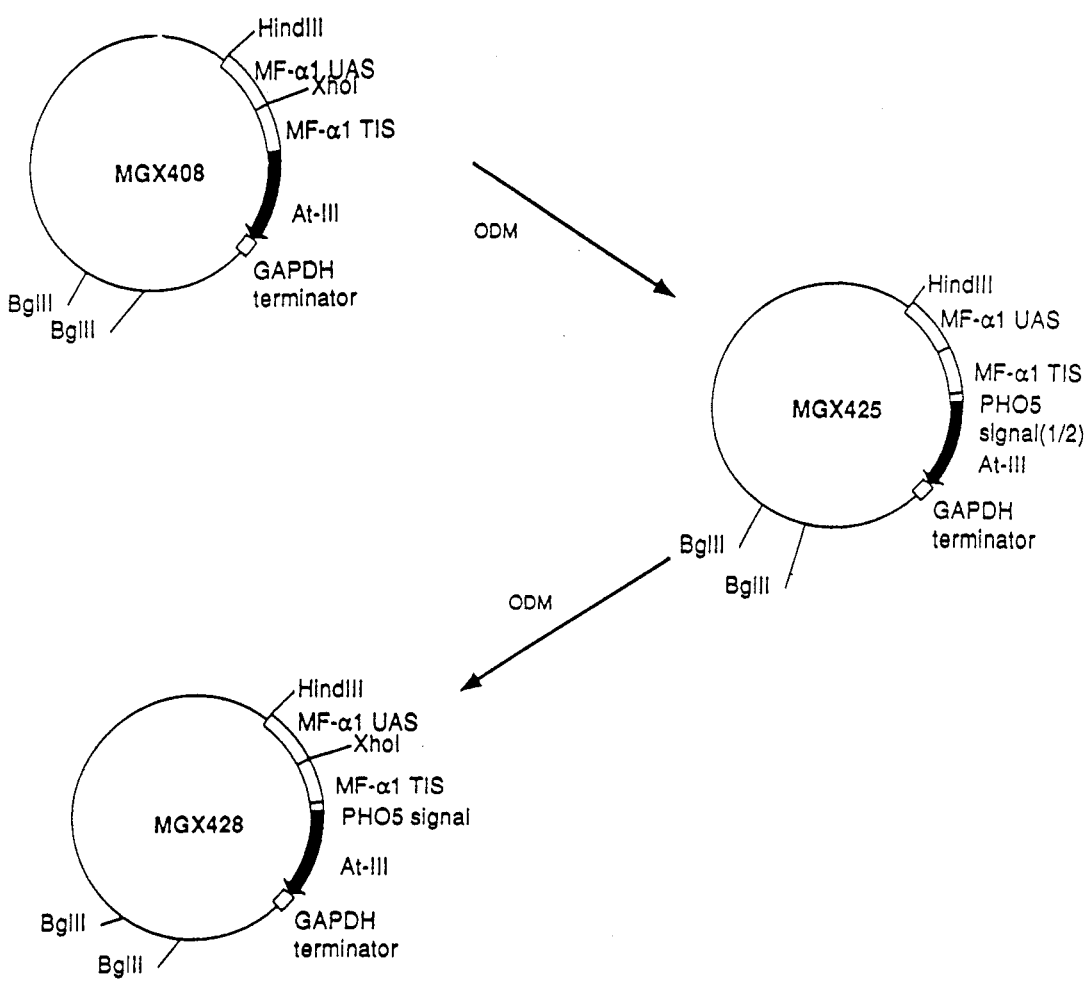

FIG. 19 is a flow chart showing the assembly of a gene encoding the PHO5 signal and the structural gene for At-III.

Figure 20:
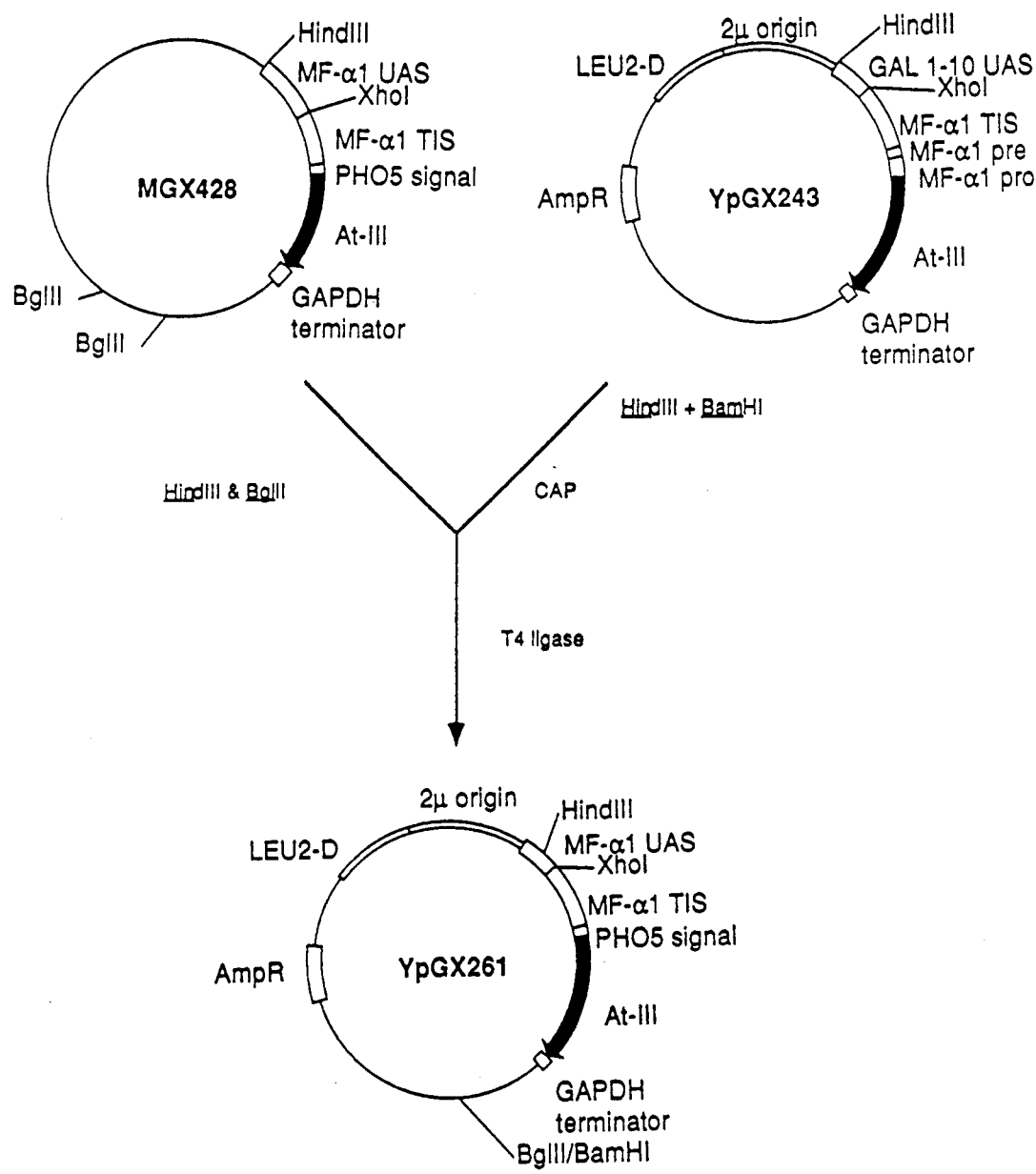

FIG. 20 is a flow chart showing the assembly of a yeast-E. coli shuttle vector including the PHO5 signal-/At-III gene.

Figure 21:
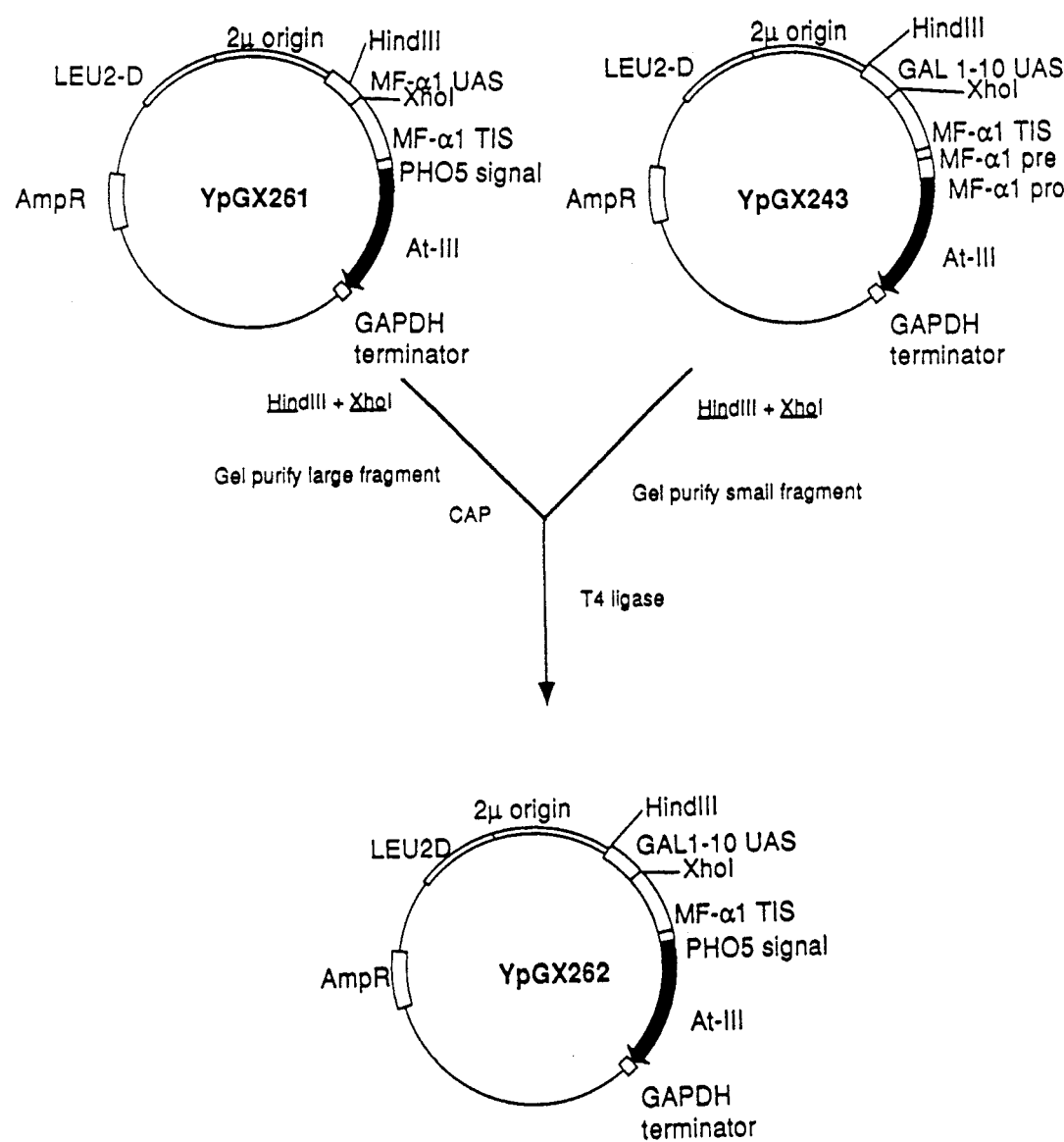

FIG. 21 is a flow chart showing the assembly of a galactose-regulated PHO5 signal/At-III gene.

Figure 22:
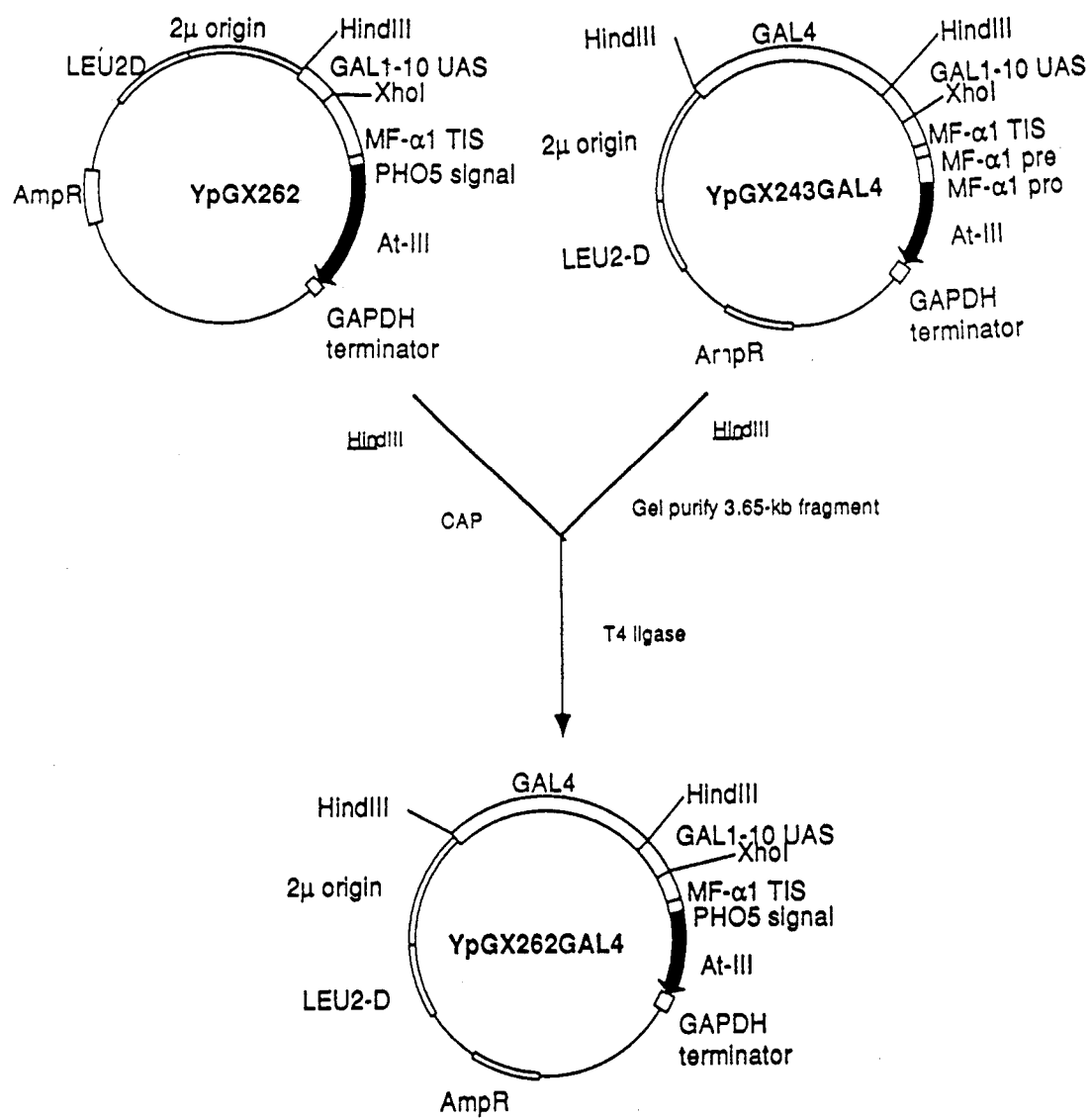

FIG. 22 is a flow chart showing the addition of the GAL4 gene to the plasmid YpGX262.

Figure 23:
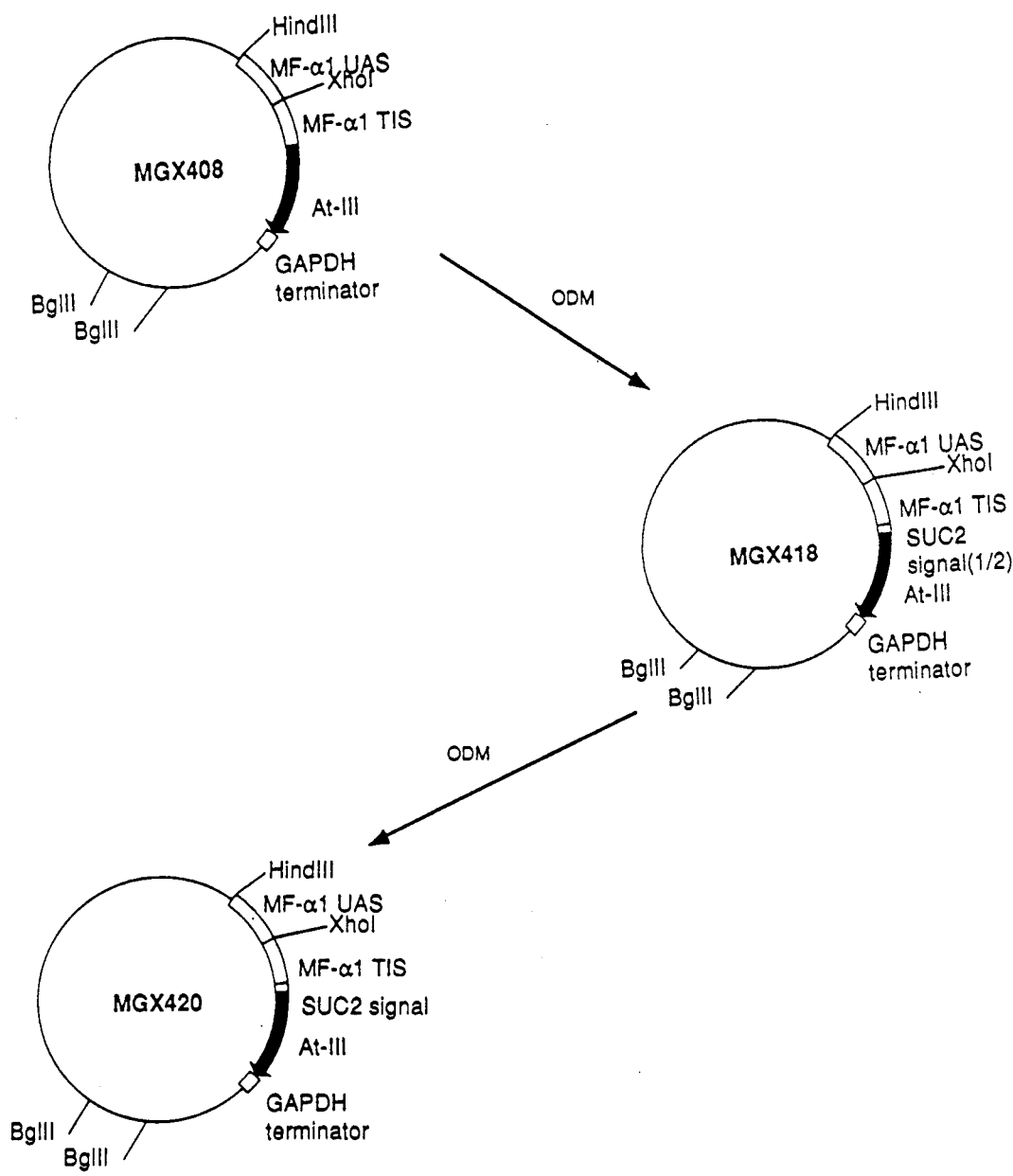

FIG. 23 is a flow chart showing the assembly of a gene encoding SUC2 signal-At-III.

Figure 24:
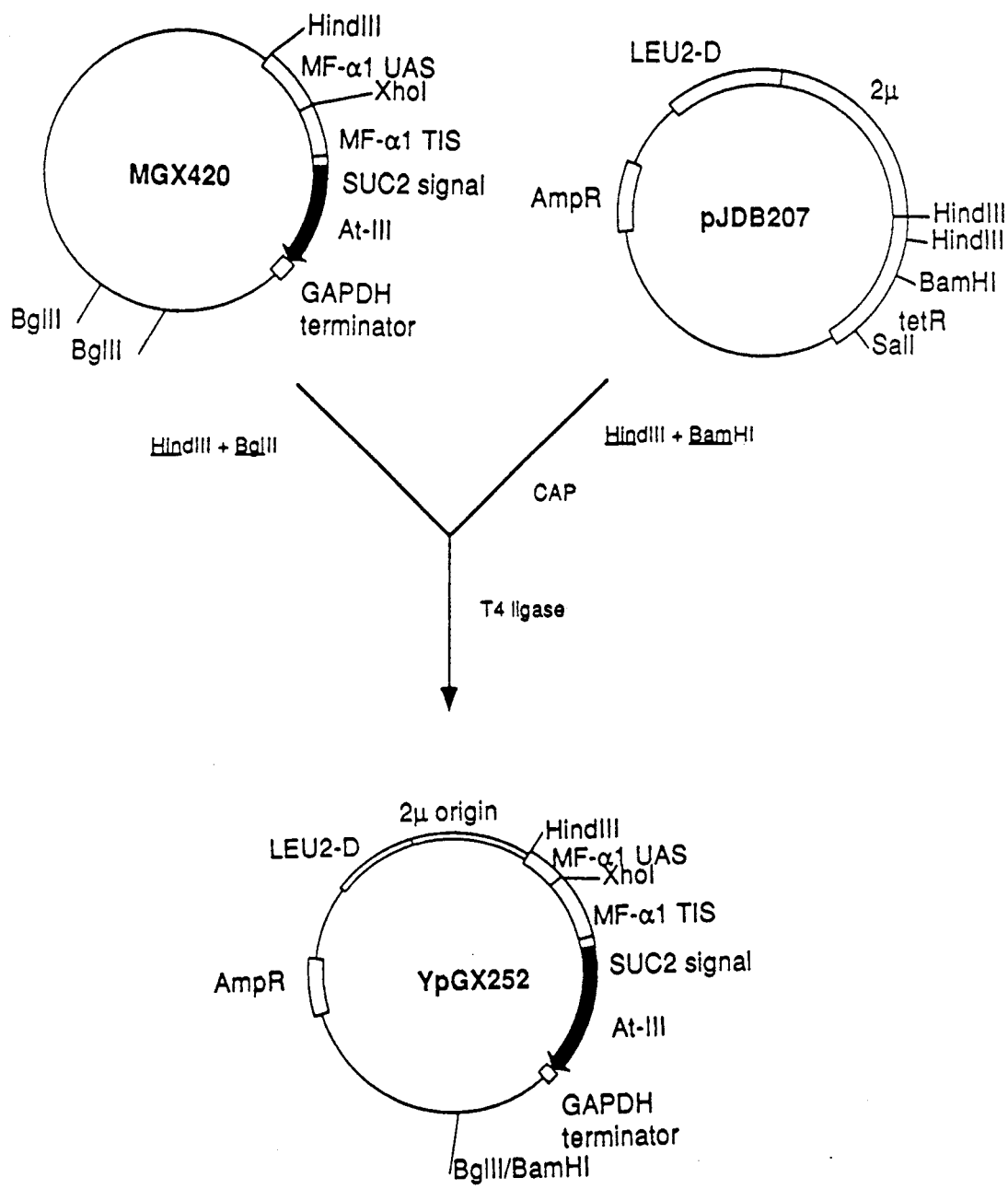

FIG. 24 is a flow chart showing the assembly of a yeast-E. coli shuttle vector including the SUC2 signal-At-III gene.

Figure 25:
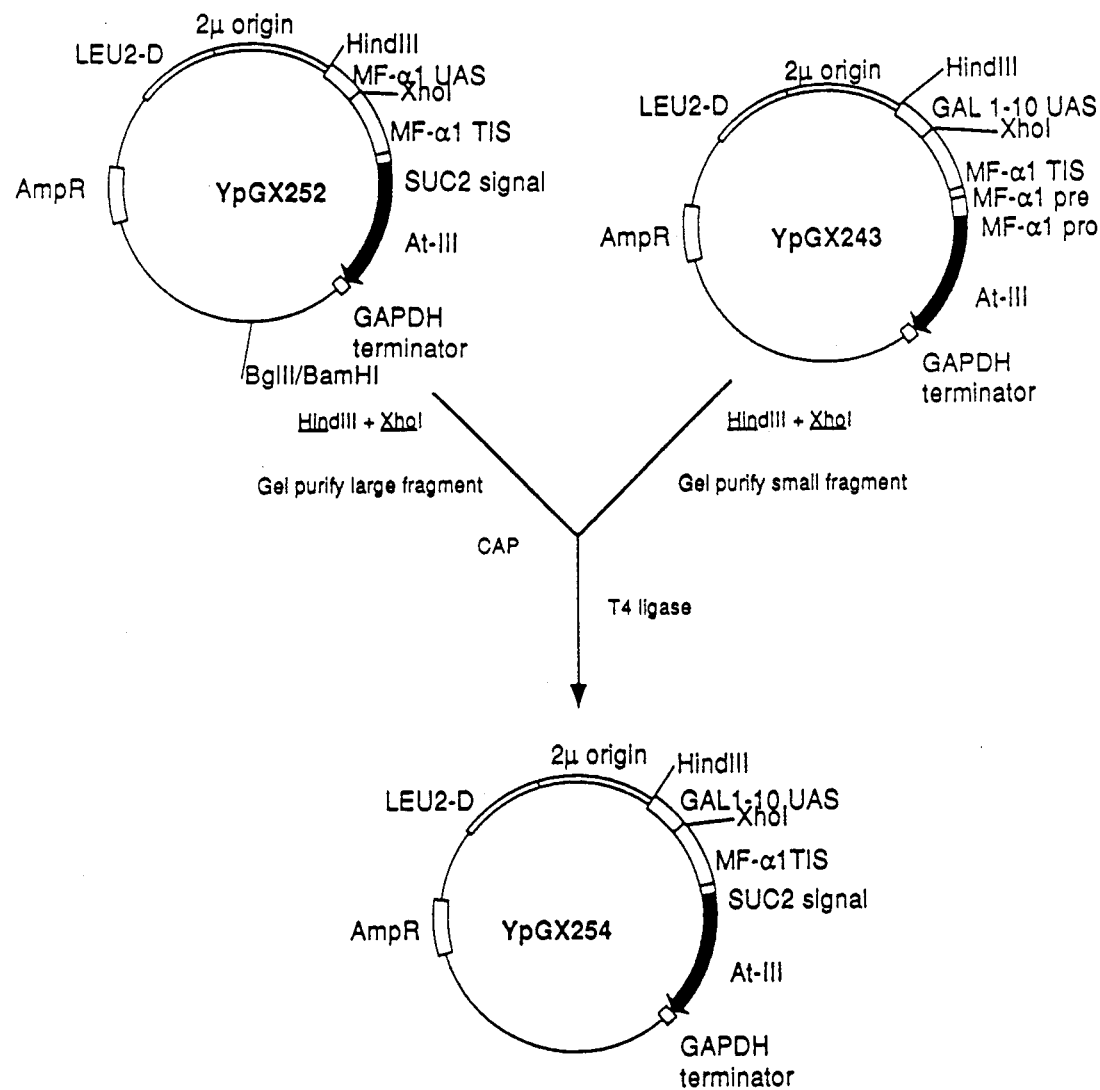

FIG. 25 is a flow chart showing the assembly of a galactose-regulated SUC2 signal-At-III gene.

Figure 26:
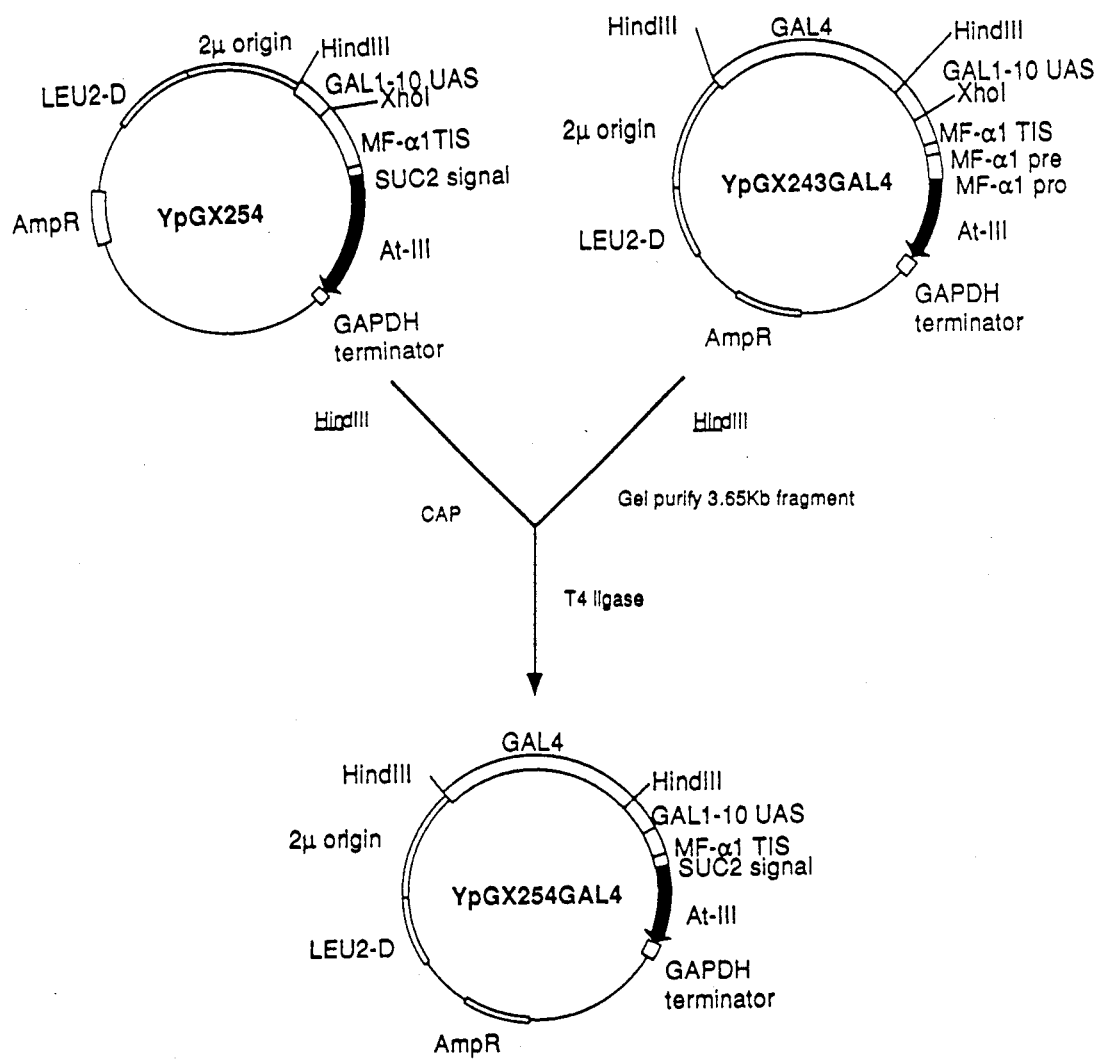

FIG. 26 is a flow chart showing the addition of the GAL4 gene to YpGX254.

Figure 27:
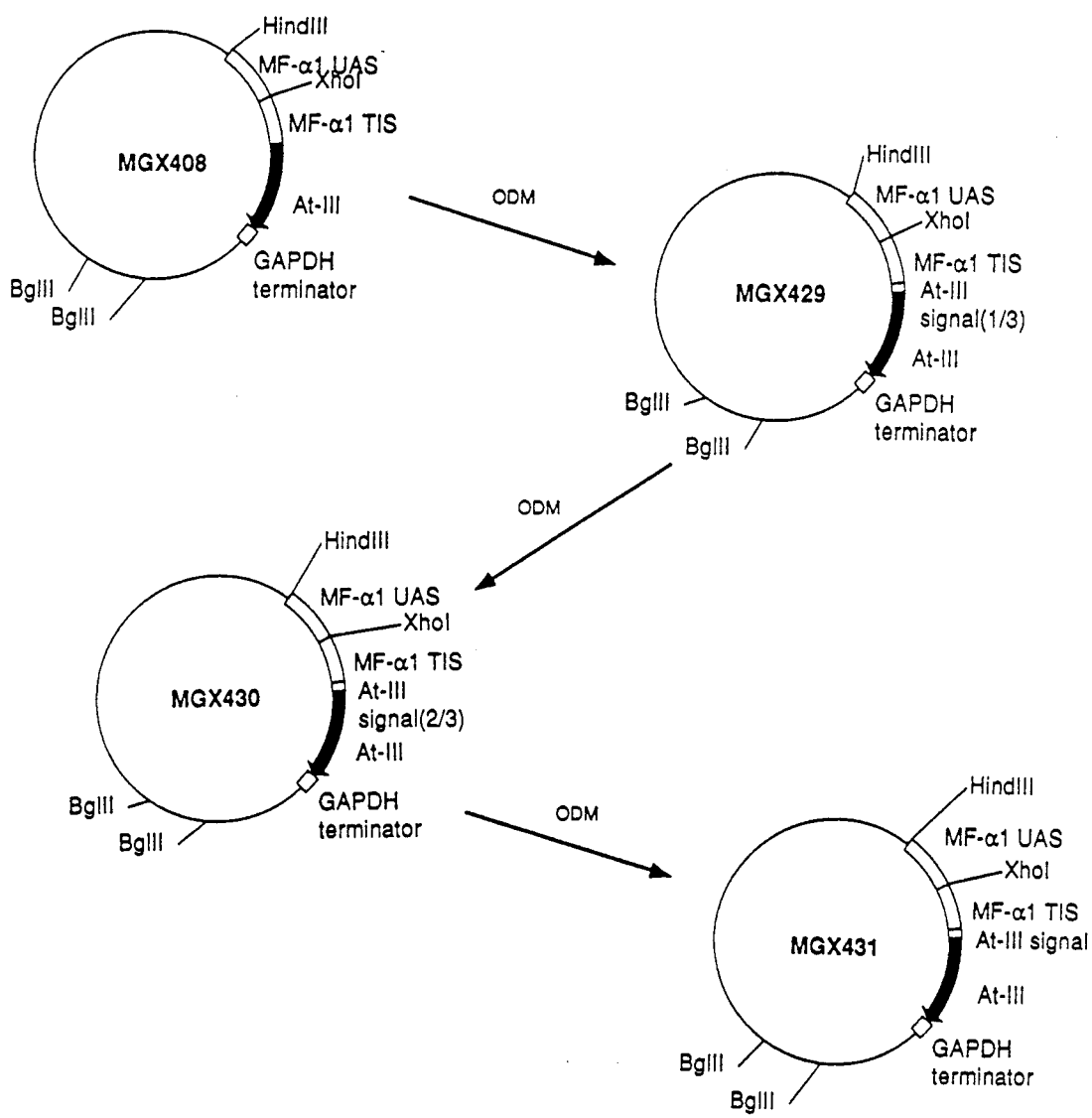

FIG. 27 is a flow chart showing the assembly of a gene encoding pre-At-III.

Figure 28:
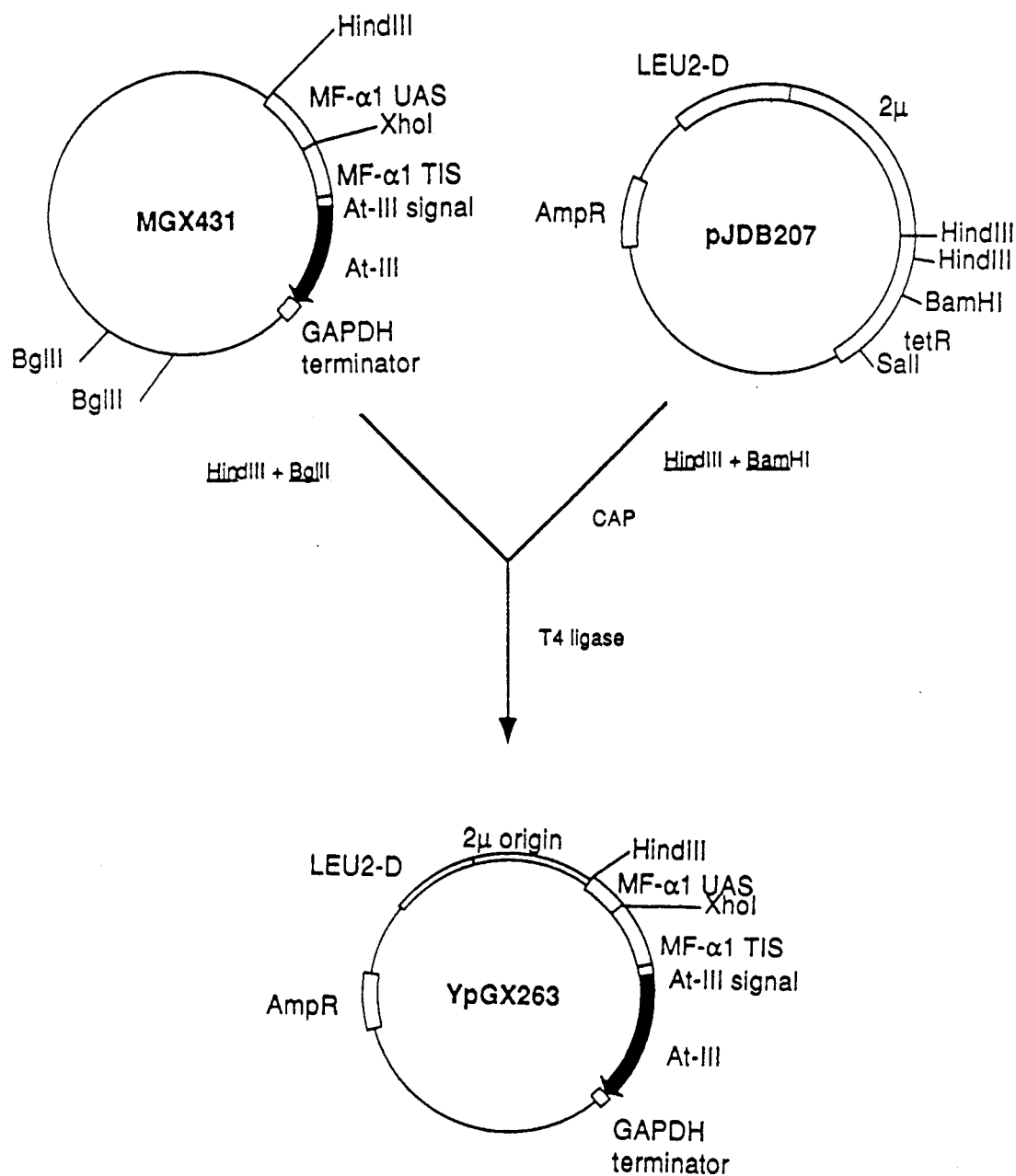

FIG. 28 is a flow chart showing the assembly of a yeast-E. coli shuttle vector including the pre-At-III gene.

Figure 29:
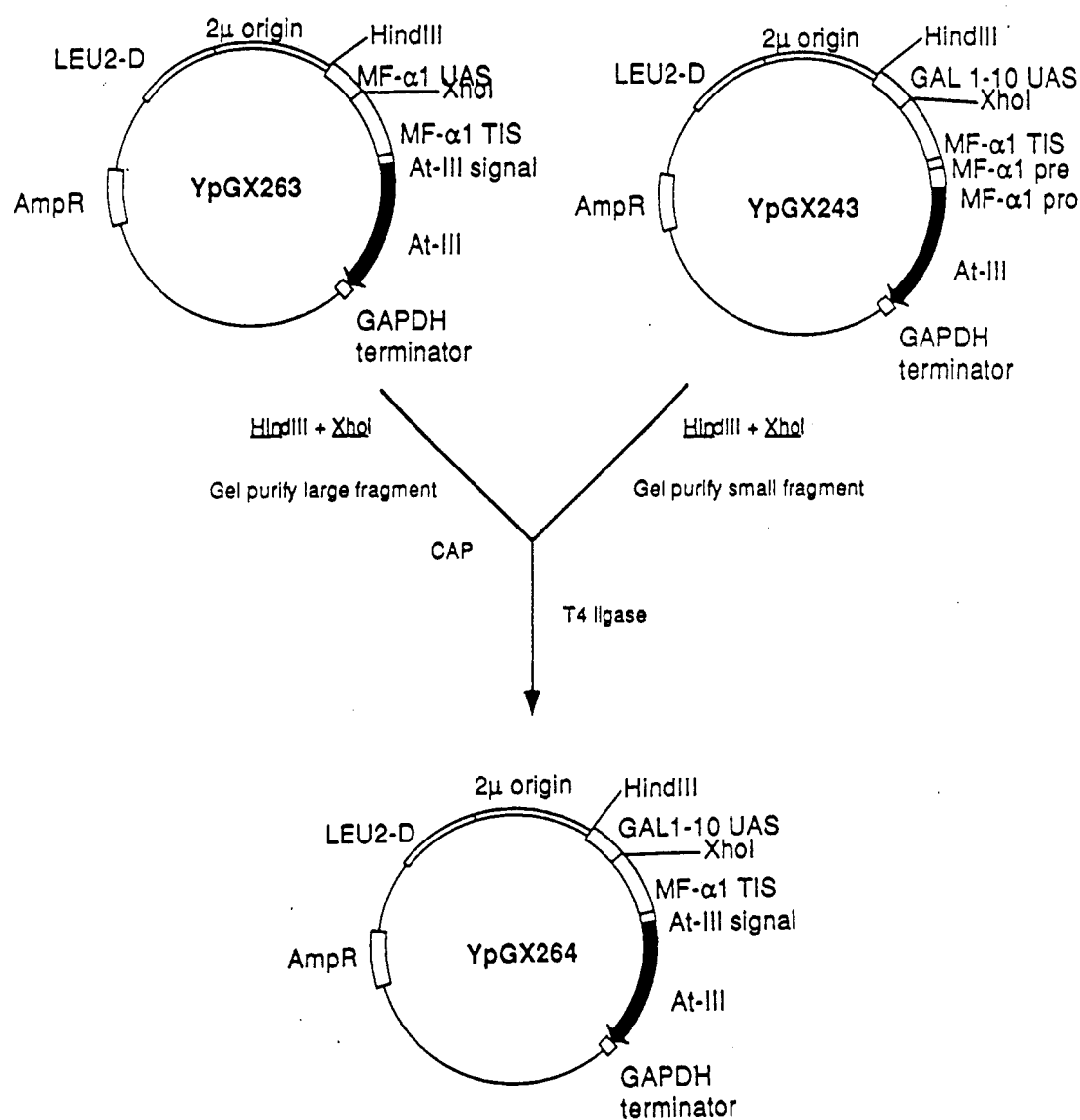

FIG. 29 is a flow chart showing the assembly of a galactose-regulated pre-At-III gene.

Figure 30:
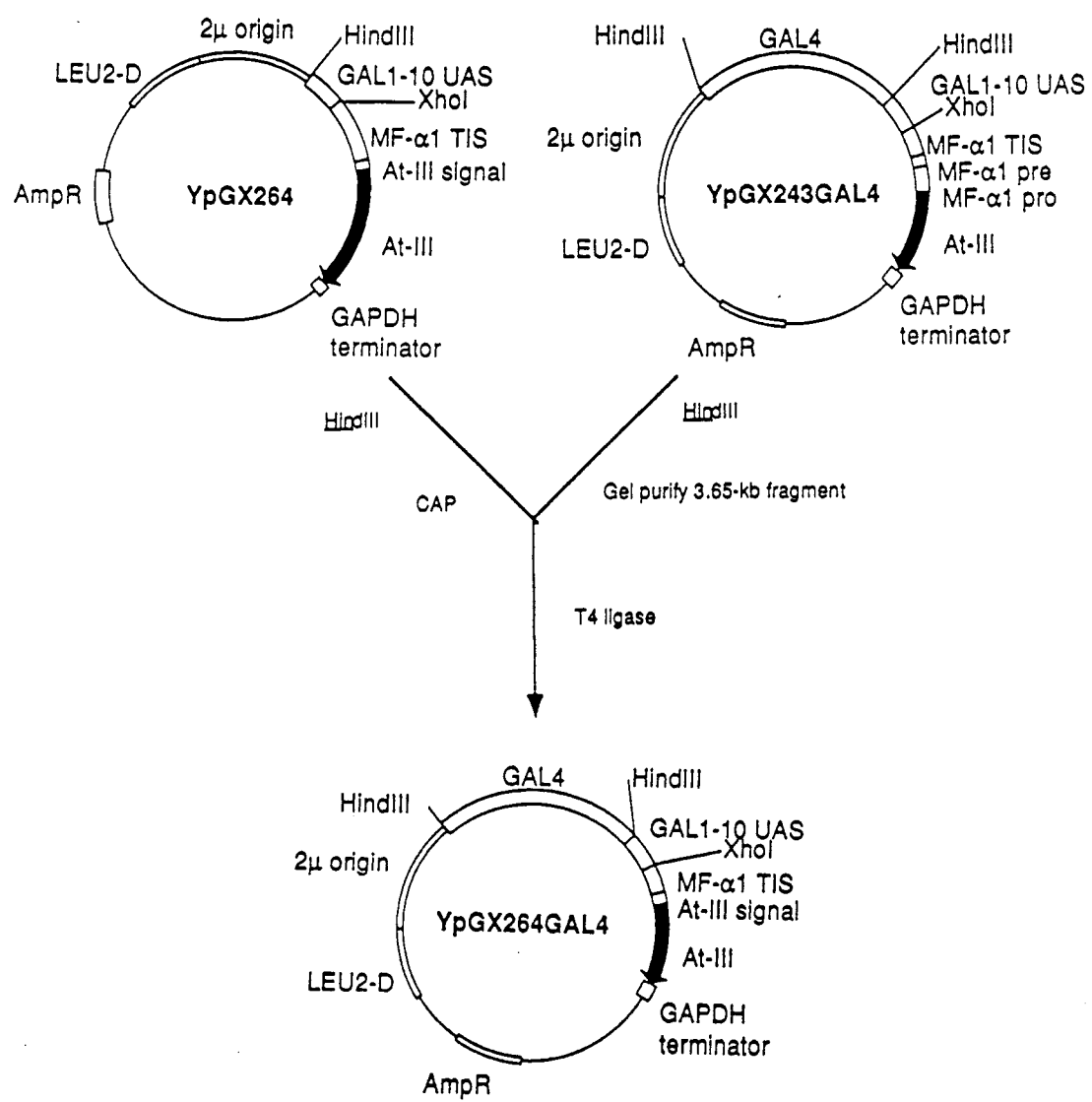

FIG. 30 is a flow chart showing the addition of the GAL4 gene to YpGX264.

Figure 31:
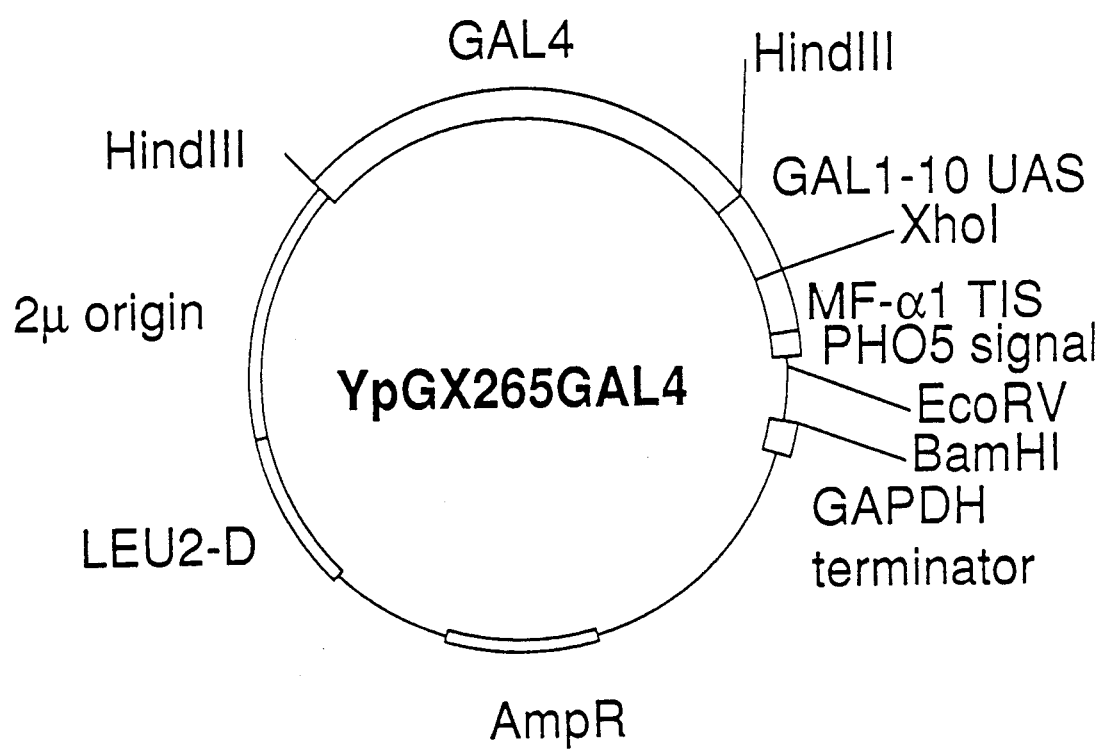

FIG. 31 shows a restriction and functional map of a yeast-E. coli shuttle vector, plasmid YpGX265 GAL4. Note that the XhoI, EcoRV and BamHI sites are not unique in this plasmid.

Figure 32:
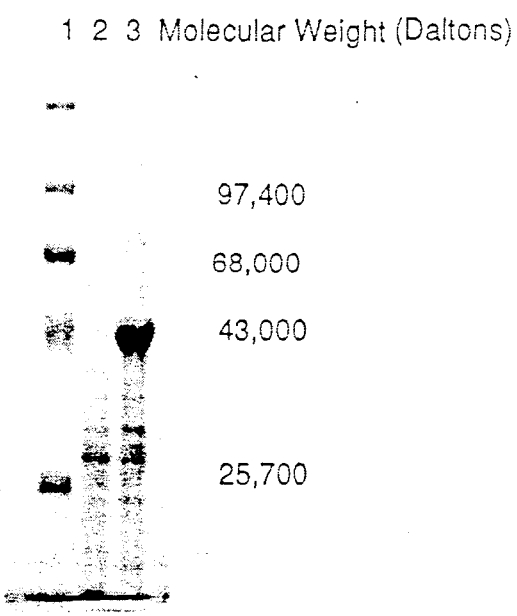

FIG. 32 shows the detection of PHO5 signal-At-III protein by Coomassie staining of an SDS-polyacrylamide gel. Lane 1, molecular weight standards; Lane 2, PHO5 signal-At-III, insoluble YPD, strain D8(YpGX262GAL4); Lane 3, PHO5 signal-At-III, insoluble, YPGal, strain D8 (YpGX262GAL4).

FIG. 33 shows bases −158 to −1 of MF-α-1. Kurjan et al., *Cell* 30:933-943 (1982).

Figure 34:
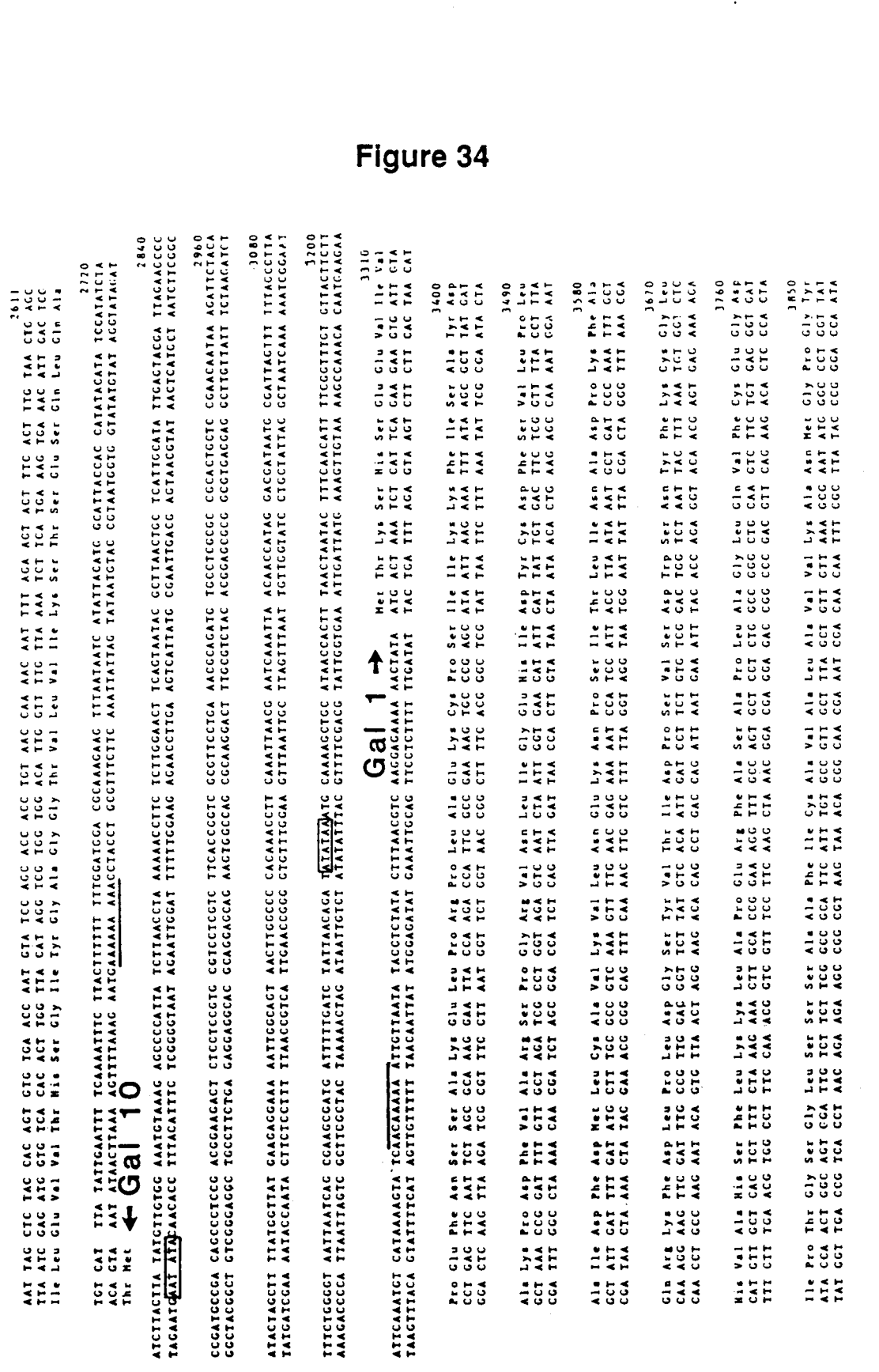
Figure 34:
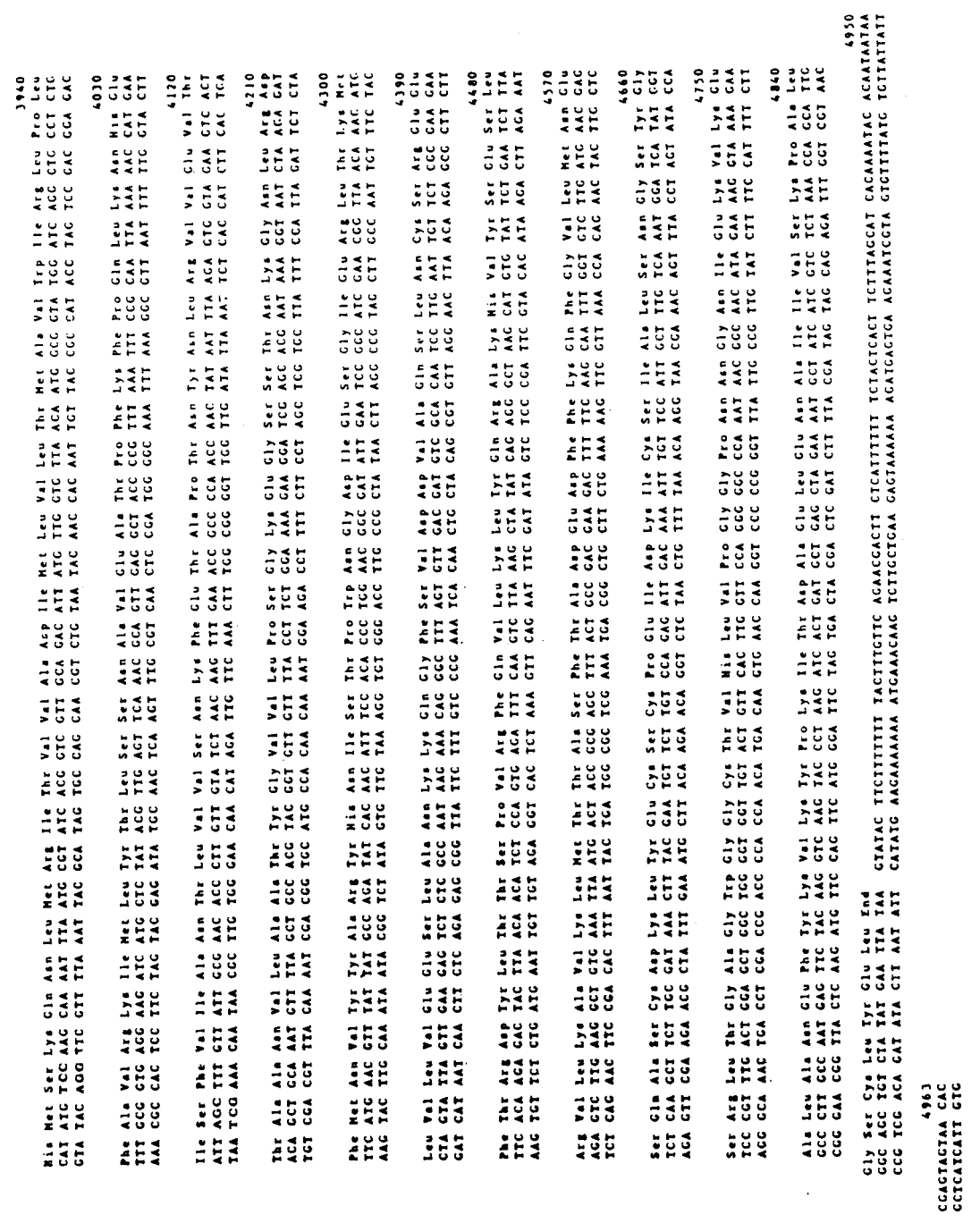

FIG. 34 shows bases −610 to −157 of the Saccharomyces GAL region, taking the A of the GAL1 ATG translation start codon as position +1. Citron et al., *J. Bacteriol.* 158:269-278 (1984).

DESCRIPTION OF THE PREFERRED EMBODIMENTS

In the following description, reference will be made to various methodologies well known to those of skill in the art of recombinant genetics. Publications and other materials setting forth such well known methodologies will be referred to in the course of this description, and are incorporated herein by reference in their entireties as though set forth in full. Standard reference works setting forth the general principles of recombinant DNA technology include Lewin, B. M., *Genes II*, John Wiley & Sons, Publishers, N.Y. (1985). The molecular biology of the yeast Saccharomyces is comprehensively reviewed in Strathern, J. N. et al., *The Molecular Biology of the Yeast Saccharomyces: Life Cycle and Inheritance*, Cold Spring Harbor Laboratory, Publisher, N.Y. (1981) and Strathern, J. N. et al., *The Molecular Biology of the Yeast Saccharomyces: Metabolism and Gene Expression*, Cold Spring Harbor Laboratory, Publisher, N.Y. (1982).

By "DNA expression vector" is meant any autonomous element capable of replicating in a host independently of the host's chromosome, after additional sequences of DNA have been incorporated into the autonomous element's genome. Such DNA expression vectors include bacterial plasmids and phages and yeast plasmids. Plasmids may be single or multi copy, with multi copy plasmids preferred.

By "ultrahigh expression" is meant the production of heterologous polypeptide in a yeast host at levels not less than one gram per liter of yeast culture and not less than 10% of total yeast cell protein. It will be appreciated that it may be desirable to control the expression of certain heterologous polypeptides that are toxic to the host's cells at sub-ultrahigh levels. This may be accomplished, for example, by including within the expression vector a DNA sequence capable of repressing expression in the presence of a factor such as a gene product or metabolite, while maintaining the ability to express at ultrahigh levels in the absence of that gene product or metabolite.

By "in phase" is meant that the nucleotide sequence of interest is in the same reading frame as those nucleotide sequences to which the sequence of interest may be operably linked.

By "promoter" is meant a DNA sequence generally described as the 5' region of a gene, located proximal to the start codon. At the promoter region, transcription or expression of an adjacent gene is initiated. This is called the transcription initiation site. Also at the promoter region may be a sequence of nucleotides that interacts with a positive intermediary, thereby exerting positive control over the expression of any operably linked structural gene or genes. A preferred positive intermediary for the purposes of the present invention is the protein produced by the GAL4 structural gene. In a "hybrid yeast promoter," the transcription initiation site and the nucleotide sequence which interacts with a positive intermediary are derived from different yeast genes.

By "functional segment" is meant the DNA sequence or sequences responsible for effecting the function attributed to the fragment of interest.

By "galactose inducible" is meant a structural gene the expression of which is inducible by the presence in the medium of galactose. The regulation of yeast galactose genes is described by Oshima, "*Regulatory Circuits* for Gene Expression: The metabolism of Galactose and Phosphate," in, J. Strathern et al., eds., *The Molecular Biology of the Yeast Saccharomyces: Metabolism and Gene Expression*, Cold Spring Harbor Laboratory, Publisher, N.Y., pp. 159-180 (1982). Preferred for the purposes of the present invention, are the Leloir pathway enzymes galactokinase, transferase and epimerase, coded for by genes designated GAL1, GAL7 and GAL10, respectively, and the specific galactose regulatory protein, coded for by the GAL80 gene. It will be appreciated that any DNA sequence capable of binding the GAL4 protein, whether natural or synthetic, and including consensus binding sequences, may be used for the purposes of the present invention and is included within the scope thereof. Specific DNA binding of the GAL4 protein and a near-consensus synthetic oligonucleotide are described in Giniger et al., *Cell* 40:767-774 (1985). Shimada et al., *Gene* 39:1-9 (1985) describe the inducible expression of the GAL80 gene by the GAL4 protein. GAL1 and GAL10 are herein referred to collectively as GAL1-10. The DNA sequence of the promoter region that interacts with the positive intermediary as described above is also termed the "upstream activation site" (UAS). Also preferred for the purposes of the present invention is the upstream activation site of the GAL1-10 gene comprising bases $-613$ to $-158$.

By "structural gene" is meant a DNA sequence that may be transcribed into mRNA, which mRNA may then be translated into a sequence of amino acids characteristic of a specific peptide. Typically the first nucleotide of the first translated codon is numbered $+1$, and the nucleotides are numbered consecutively with positive integers throughout the translated region of the structural gene and into the 3' untranslated region. The numbering of nucleotides in the promoter and regulatory region 5' to the translated region proceeds consecutively with negative integers. Thus the 5' nucleotide of the promoter and regulatory region adjacent to the first translated nucleotide of the structural gene would be numbered $-1$.

By "operably linked" is meant that the promoter controls the initiation of expression of the polypeptide encoded by the structural gene.

By "transcription initiation site" (TIS) is meant a DNA sequence of a promoter to which RNA-polymerase binds, thereby initiating transcription of succeeding codons in a 5' - 3' direction. For the purposes of the present invention, a transcription initiation site of a highly expressed yeast gene is used. Those of skill will appreciate that many such highly expressed yeast genes are known, the transcription initiation sites of which are suitable for the purposes of the present invention. Preferred for the present invention is the transcription initiation site of an alpha mating factor gene. The alpha mating factor gene of yeast and yeast mating types are described in Herskowitz et al., "Control of Cell Type in *Saccharomyces cerevisiae*: Mating Type and Mating-Type Interconversion," in, J. Strathern et al., eds., *The Molecular Biology of the Yeast Saccaromyces: Life Cycle and Inheritance*, Cold Spring Harbor Laboratory, Publisher, N.Y., pp. 181-209 (1981); Nasmyth, *Ann. Rev. Genet.* 16:439-500 (1982). Preferred for the purposes of the present invention is the gene encoding the alpha-1 mating factor (MF-alpha-1). Also preferred for the purposes of the present invention is the transcription initiation site of the MF-alpha-1 gene comprising bases $-158$ to $-3$.

By "signal sequence" is meant that part of the DNA sequence encoding the prepro- or pre-protein, which has a high affinity to biomembranes or special receptor-proteins in biomembranes or which is involved in the transport or translocation of prepro- or pre-protein. These transport or translocation processes are often accompanied by processing of the prepro- or pre-protein to create the mature form of the protein. Preferred for the purposes of the present invention, is a signal sequence derived from the DNA sequence encoding yeast acid phosphatase. Phosphatase genes are described in Oshima, "Regulatory Circuit for Gene Expression: The Metabolism of Galactose and Phosphate," in, J. Strathern et al., eds., *The Molecular Biology of the Yeast Saccharomyces: Life Cycle and Inheritance*, Cold Spring Harbor Laboratory, Publisher, N.Y., pp. 159-180 (1982). More preferred is the DNA sequence encoding repressible acid phosphatase (PHO5) gene. Even more preferred as a signal sequence for the purposes of the present invention is the nucleotide sequence:

ATGTTCAAATCTGTTGTTTACTCTATTTTGGCTGCTTCTTTGGCCA
ACGCT.

By "preferred yeast codons" is meant codons containing nucleotide bases that have been observed more frequently than other possible codon triplets to encode particular amino acids in yeast. Preferred yeast codons and their use are described by Holland et al., *J. Biol. Chem.* 255:2596-2605 (1980).

By "transcription terminator" is meant a sequence of DNA, presented at the end of the transcript, that causes RNA polymerase to terminate transcription. Preferred for the purposes of the present invention is the transcription terminator of a yeast glyceraldehyde-3-phosphate dehydrogenase gene (GAPDH). The GAPDH gene is described in Holland et al., *J. Biol. Chem.* 254:9839-9845 (1979). Also preferred as a transcription terminator for the purposes of the present invention is the nucleotide sequence:

GGATTCCGGGTTTTTTATAGCTTTATGACTTAGTTTCAATTATATA
CTATTTTAATGACATTTTCAG.

By "replicon" is meant a unit of genome in which DNA is replicated, and which contains an origin for initiation of replication (replication origin). Preferred replicons for the purposes of the present invention include fragments of the yeast 2 micron plasmid, termed YEp plasmid vectors, but other replicons such as YIp, YRp and YCp may also be used. These are described, for example, in Botstein et al., "Principles and Practice of Recombinant DNA Research with Yeast," in, J. Strathern et al., eds., *The Yeast Saccharomyces: Metabolism and Gene Expression*, Cold Spring Harbor Laboratory, Publishers, N.Y., pp. 607-636 (1982). Also preferred for the purposes of the present invention is a replicon derived from plasmid pJDB207. This plasmid is available from commercial sources such as Amersham Corporation, Arlington Heights, Ill., 60005.

By "selectable yeast marker" is meant a gene conferring upon the cell in which it is contained the ability to grow in a medium which either contains or lacks a particular constituent. Thus, for example, a gene conferring ability to grow in the absence of a required nutrient, such as a particular amino acid, would act as a selectable marker. If this gene is not normally present in the yeast cell, it may be introduced via, for example, a plasmid. Thus, only clones containing the plasmid would be able to grow in a medium that lacked the required nutrient. Use of selectable markers is described in Broach et al., Gene 8:121-133 (1979). Common selectable yeast markers include LEU2, URA3, TRP1, ARG4 and HIS3 genes. Preferred for the purposes of the present invention is the LEU2 gene. More preferred is the LEU2-d gene. Different markers are used for bacteria such as E. coli. Here, genes are chosen which confer upon the host bacterium resistance to an antibiotic. Commonly employed selectable markers for bacteria are genes conferring resistance to ampicillin and tetracycline. A plasmid that is constructed to contain selectable markers for both yeast and bacteria will be capable of selection in either host. Because such a plasmid is capable of expression in either yeast or bacteria, it is termed a "shuttle vector." Also preferred for the purposes of the present invention is a selectable yeast marker derived from plasmid pJDB207. This plasmid is available from commercial sources such as Amersham Corporation, Arlington Heights, Ill., 60005.

By "target peptide" is meant the peptide it is desired to express in the yeast host according to the present invention. The target peptide may be encoded by a structural gene, in which case a mature peptide product would be expressed. Alternatively, the target peptide may comprise the prepro-, pro- or pre- forms of the peptide. The target peptide will be "heterologous" if it is encoded by a DNA sequence that is foreign, i.e., originates from a donor different from the host or is a chemically synthesized gene, and can include a donor of a different species from the host. The heterologous gene codes for a peptide ordinarily not produced by the organism. A "homologous" target peptide is encoded by a DNA sequence originating from the host, which sequence encodes a peptide ordinarily produced by the organism.

By "integrated to yeast chromosomal material" is meant that the DNA sequence of interest is caused or allowed to become part of the chromosomal material of the yeast host itself, and is replicated along with host chromosomal replication, as opposed to replicating independently as when the DNA sequence of interest is carried in a DNA expression vector such as a plasmid. Integration may be effected, for example, by employing an integrating vector such as YIp5. YIp5 is described, for example, by Botstein et al., "Principles and Practice of Recombinant DNA Research with Yeast," supra.

By "transformation" is meant the acquisition in eukaryotic cells of new genetic markers by incorporation of added DNA. This is the process by which naked DNA is introduced into a cell, resulting in a heritable change. The transformation of yeast is described in Hinnen et al., Proc. Natl. Acad. Sci. USA 75(4): 1929-1933 (1978).

In a preferred embodiment, the present invention provides for a DNA expression vector which can be used to express many heterologous proteins at ultrahigh expression levels of no less than 1 gram per liter of yeast culture or at least 10% of total yeast cell protein. In this embodiment, the hybrid yeast promoter was composed of elements from two naturally occuring yeast promoters. The transcription initiation site was derived from the MF-alpha-1 gene. An upstream activation site derived from the regulatory region of the yeast GAL1-10 gene was utilized in place of the MF-alpha-1 upstream activation site. Use of the GAL1-10 upstream activation site permits tightly regulated expression of the MF-alpha-1 transcription initiation site by metabolites such as glucose and galactose. The hybrid yeast promoter was carried on a yeast-E. coli shuttle vector derived from the plasmid pJDB207. Beggs, "Multiple-Copy Yeast Plasmid Vectors," in, D. von Wettstein et al., eds, Molecular Genetics in Yeast, Alfred Benzon Symposia, vol. 16, pp. 383-389 (1981). Because this shuttle vector carries the combination of a yeast 2 micron plasmid replication origin and the LEU2-d selectable yeast marker, plasmid copy number is very high in yeast (up to about 200 copies per haploid cell). Using this vector, however, it was found that target peptide expression directed by the hybrid GAL1-10/MF-alpha-1 promoter was limited.

It was determined by the present inventors that the disappointingly low expression directed by the hybrid GAL1-10/MF-alpha-1 promoter was caused by insufficient GAL4 protein in the yeast host cell. The GAL4 protein, encoded by the GAL4 gene, is a positive regulatory protein for the yeast galactose system. It has been shown that this protein binds to the GAL1 upstream activation site and is required for high level regulated expression of the GAL1 gene. The amount of GAL4 protein is normally very low in the yeast cell. Laughon et al., Proc. Natl. Acad. Sci. USA 79:6827-6831 (1982). Inclusion of the GAL4 structural gene in the DNA expression vector apparently increased the amount of GAL4 protein in the cell and enhanced expression directed by the plasmid-borne hybrid promoter.

To terminate transcription efficiently, the plasmid of this embodiment carries a synthetic yeast transcription terminator designed from a yeast GAPDH gene. The synthetic DNA sequence was designed by the present inventors employing convenient restriction endonuclease recognition sites to facilitate DNA manipulations. The use of restriction endonucleases and associated molecular biology techniques are described in Maniatis et al., Molecular Cloning: A Laboratory Manual, Cold Spring Harbor Laboratory, Publisher, N.Y. (1982).

A signal sequence derived from the yeast PHO5 gene was inserted between the hybrid promoter and the start of the coding sequence of the target peptide. The signal sequence employed was designed from the yeast PHO5 gene and comprised a synthetic DNA sequence, such that the codon selection was based on preferred yeast codons rather than the naturally occuring PHO5 signal sequence.

As a result of these modifications, the present inventors found that this DNA expression vector was capable of ultrahigh levels of heterologous target peptide expression unprecedented in the art of yeast expression. This surprisingly ultrahigh expression could not have been predicted, and is greatly in excess of the improvements in expression that would be expected from the known additive effects of the individual alterations.

In another preferred embodiment, the invention comprises a DNA expression system comprising a DNA expression vector prepared as follows:

1. A novel hybrid promoter that includes the efficient transcription initiation site (including bases −158 to −1) of the MF-alpha-1 gene, Kurjan et al., *Cell* 30:933-943 (1982), and a GAL4 binding site derived from the GAL1-10 regulatory region, Citron et al., *J. Bacteriol.* 158:269-278 (1984), including bases −610 to −157. (The A of the GAL1 ATG translation start codon is +1.) This hybrid regulatory region was constructed by placing a XhoI restriction endonuclease site at base number −158 preceding the ATG translational start of the MF-alpha-1 gene, and HindIII and XhoI restriction sites at bases −610 and −157 of the GAL1-10 regulatory region, respectively.

2. A PHO5 (Arima et al., *Nucleic Acids Res.* 11:1657-1672 (1983)) signal encoding sequence derived from synthetic DNA, substantially comprising preferred SaccharomYces codons rather than the natural coding sequence. The synthetic DNA sequence encoding this signal is:

```
ATGTTCAAATCTGTTGTTTACTCTATTTTGGCTGCTTCTTTGGCCA
ACGCT.
```

3 A GAPDH (Holland et al., *J. Biol. Chem.* 254:9839-9845 (1979); Holland et al., *J. Biol. Chem.* 255:2596-2605 (1980)) transcription terminator derived from synthetic DNA. The sequence of this strong transcription terminator is:

```
GGATCCCGGGTTTTTTATAGCTTTATGACTTAGTTTCAATTATATA
CTATTTTAATGACATTTTCAG.
```

4. The Saccharomyces GAL4 (Johnston et al., *Proc. Natl. Acad. Sci. USA* 79:6971-6975 (1982)) gene to provide additional GAL4 protein to recognize the GAL4 binding sites on the plasmid.

5. Yeast and *E. coli* replicating origins and selectable markers derived from plasmid pJDB207. Beggs, J.D. "Multiple-copy yeast plasmid vectors," in, Alfred Benzon Symposium 16, *Molecular Genetics in Yeast*, Von Wettstein, D. et al., eds., Munksgaard, Copenhagen, pp. 383-389 (1981). The yeast replication origin derived from the 2 micron plasmid and the LEU2-d gene permit especially high plasmid copy number in Saccharomyces (up to 200 copies per cell).

6. Restriction sites are situated between the PHO5 signal encoding sequence and GAPDH transcription terminator for insertion of foreign genes.

The materials and methods used in carrying out the present invention may be more fully understood by reference to the following examples, which examples are not intended in any manner to limit the scope of the present invention.

EXAMPLE I

Construction of an Alpha-Factor/At-III Expression Vector

Human antithrombin III (At-III), a single-chain glycoprotein, is described by Bock et al., U.S. Pat. No. 4,517,294.

Vector YpGX227 is a yeast-*E. coli* shuttle vector. For replication and plasmid selection in *E. coli* the replication origin and ampicillin resistance encoding sequences for plasmid pBR322 are present.

The *S. cerevisiae* LEU2 gene permits selective maintenance of the plasmid in yeast hosts with defects in the chromosomal LEU2 gene, and also permits integration of the plasmid sequences into host chromosomal DNA.

Vector YpGX227 includes the *S. cerevisiae* alphafactor (MF-alpha-1) promoter and sequences encoding the pre, pro, and first spacer. Kurjan et al., U.S. Pat. No. 4,546,082. At the end of the first spacer encoding sequence is a naturally occuring HindIII restriction site. The strategy for constructing the alpha-factor/At-III expression vector utilized that HindIII site.

To terminate transcription, a synthetic sequence derived from a yeast glyceraldehyde-3-phosphate dehydrogenase (GAPDH) gene was utilized. The sequence of this terminator is:

```
GGATCCCGGGTTTTTTATAGCTTTATGACTTAGTTTCAATTATATA
CTATTTTAATGACATTTTCAG
```

The DNA sequence encoding the alpha-factor spacer and the N-terminus of mature alpha-factor is shown below:

```
                           HindIII
AAA AGA GAG GCT GAA GCT TGG
lys arg glu ala glu ala trp
```

Figure 1:
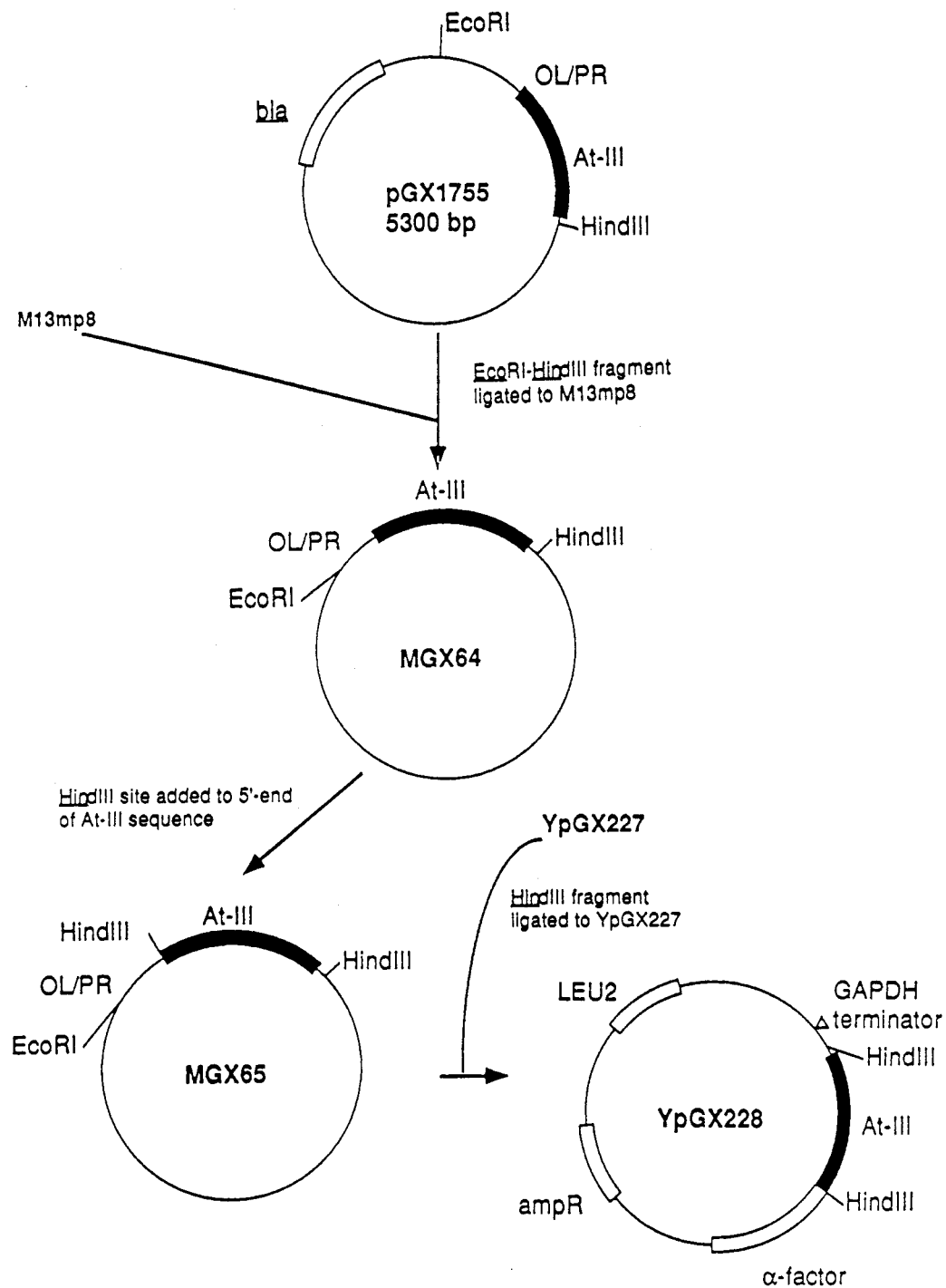
FIG. 1 is a flow chart describing the construction of At-III expression vector YpGX228.

The first step in the vector construction was to place a HindIII restriction site at the 5' end of the cloned At-III DNA sequence. This HindIII site was created by oligonucleotide-directed in vitro mutagenesis (Zoller et al., *Meth. Enzymol.* 100:468-500 (1983)) of the At-III sequence derived from the *Escherichia coli* plasmid pGX1755 (FIG. 1). Flanking the $O_L/P_R$-At-III region are unique EcoRI and HindIII restriction sites. To perform the oligonucleotide-directed mutagenesis, the EcoRI-HindIII restriction fragment containing the $O_L/P_R$ promoter and the At-III gene was first isolated from the pGX1755 and then ligated to EcoRI/HindIII-digested M13mp8. This ligation generated the M13 vector MGX64 (FIG. 1), and single-stranded MGX64 DNA was prepared following transfection of *E. coli* strain JM109.

A 39-base oligonucleotide was utilized to insert a nine-base pair sequence including a HindIII site and a trp codon at the 5' end of the At-III sequence in MGX64. Addition of two G residues following the HindIII site was necessary to create an in-frame fusion with the alpha-factor secretory sequences. This insertion created vector MGX65 whch has the following sequence at the 5' end of At-III:

```
   HindIII
   ─────
GAA GCT TGG CAC
glu ala trp his
        ─────────
        mature AT-III
```

The At-III sequence was excised from MGX65 as a HindIII fragment and ligated into the alpha-factor expression vector YpGX227 generating vector YpGX228 (FIG. 1). Vector YpGX228 carries the yeast LEU2 gene, which can be used as a selectable marker for transformation, but it does not contain a Saccharomyces origin of replication. Transformation with this plasmid therefore results in integration of the alpha-factor/At-III sequence into a yeast chromosome.

In YpGX228 the 3' end of the At-III sequence has a long transcribed, non-translated region. It has been observed that heterologous gene expression in yeast can sometimes be enhanced by positioning a yeast transcription terminator near the end of the protein coding region. Mellon et al., Gene 24:1-14 (1983). The 3' end of the AT-III DNA sequence was therefore modified by creating a BamHI restriction site immediately 3' of the TAA translation termination codon. The BamHI site was created by oligonucleotide- directed mutagenesis using MGX64 single-stranded DNA as a template and a 36-base oligonucleotide. The resulting vector, MGX66 shown in FIG. 2, has the 3' DNA sequence shown below.

```
        BamHI
        ─────
... TAA GGA TCC
    At-III
    Stop
```

Figure 2:
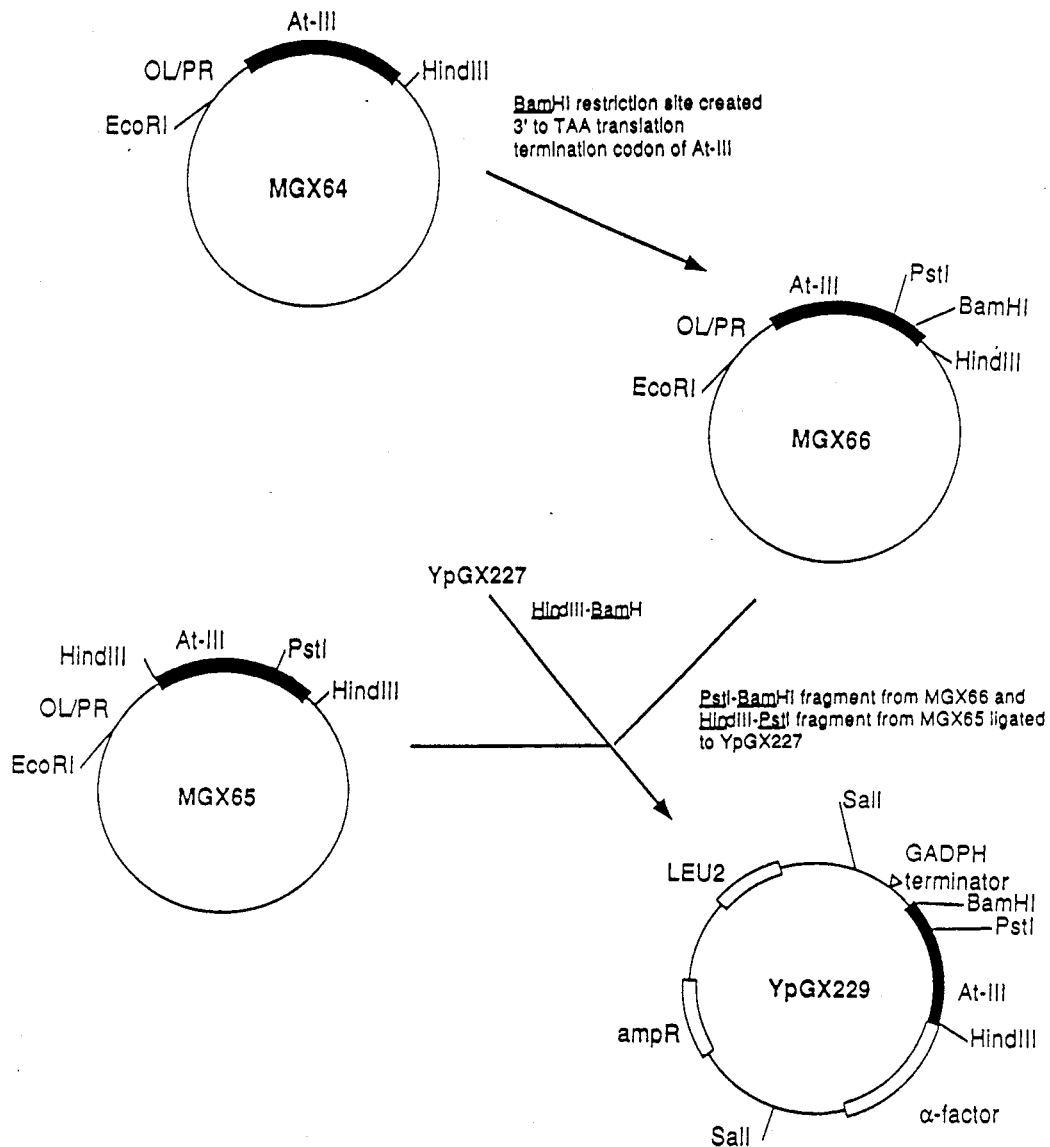
FIG. 2 is a flow chart showing the construction of expression vector YpGX229.

This BamHI restriction site can be used to link the At-III DNA sequence to the yeast glyceraldehyde-3-phosphate dehydrogenase (GAPDH) transcription termination sequence present in the alpha-factor expression vector YpGX227 (FIG. 2).

Using MGX65, MGX66 and YpGX227 (FIG. 2), an alpha-factor/At-III expression vector, YpGX229, was constructed that contains a 5' in-frame fusion of mature At-III to the first codon of the mature alpha-factor peptide and a GAPDH transcription terminator immediately 3' of the At-III coding sequence. This construction made use of the unique PstI restriction site present in the At-III DNA sequence. The 5' portion of At-III was purified from MGX65 as a HindIII-PstI restriction fragment, while the 3' portion was purified from MGX66 as a PstI-BamHI restriction fragment. The alpha-factor expression vector YpGX227 was cleaved with HindIII and BamHI, treated with calf alkaline phosphatase, and used in a threeway ligation with the At-III fragments from MGX65 and MGX66. This ligation produced vector YpGX229 (FIG. 2) in which the alpha-factor-At-III coding sequence is flanked by the alpha-factor promoter at the 5' end and the GAPDH transcription terminator at the 3' end. Because YpGX229 is derived from YpGX227, it can be used to integrate the alpha-factor/At-III sequence into a yeast chromosome.

In summary, alpha-factor/At-III expression vectors designated YpGX228 and YpGX229 were constructed that encode an alpha-factor prepro-lys-arg-glu-ala-glu-ala-trp-At-III. The alpha-factor/At-III DNA sequence from YpGX229 was chosen for further modification because it lacks the At-III 3' untranslated region and contains the GAPDH transcription terminator.

Figure 3:
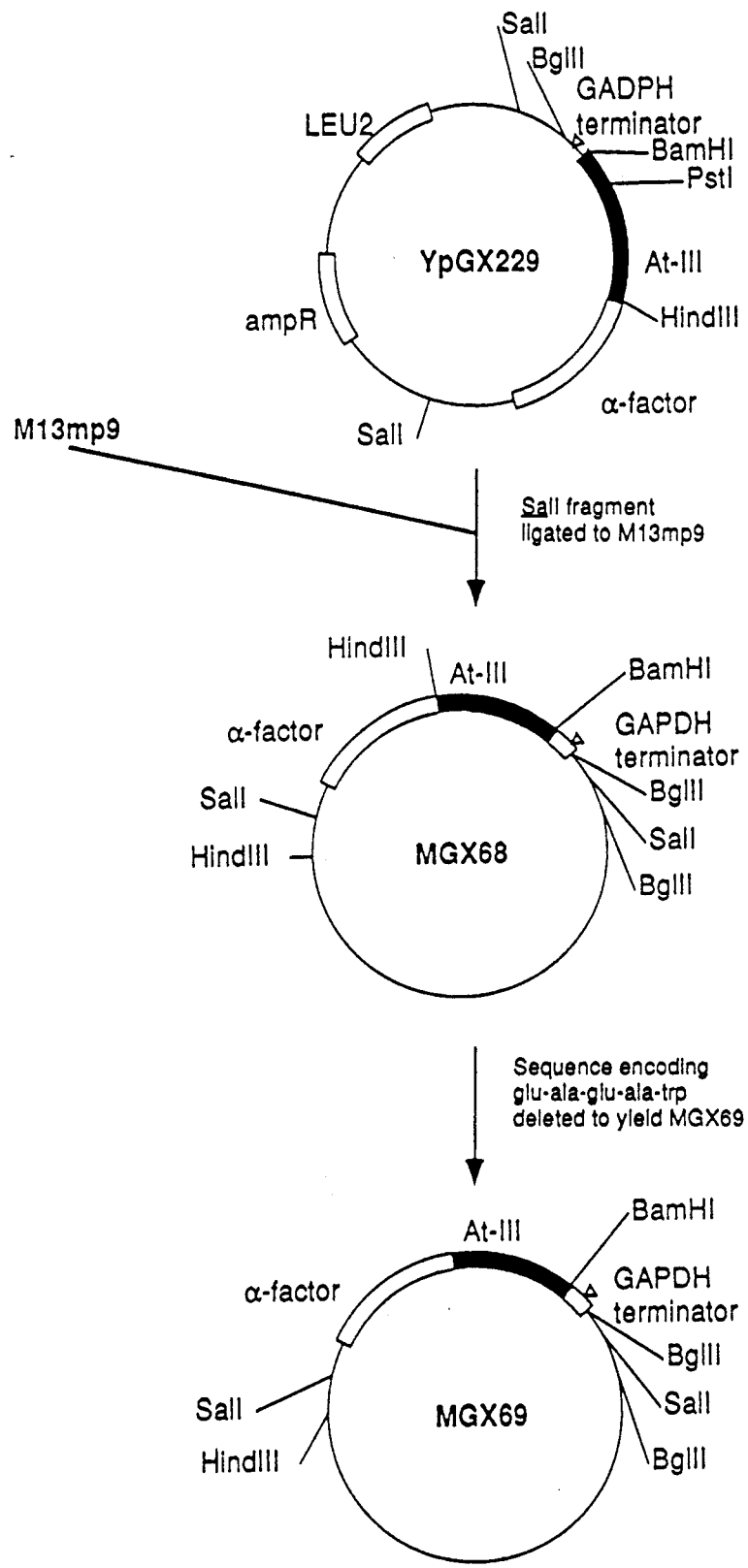
FIG. 3 is a flow chart showing the construction of M13 vector MGX69.

In order to delete the five codons separating the lys-arg codons of the alpha-factor spacer from the initial histidine codon of mature At-III, the YpGX229 alpha-factor/At-III DNA sequence was excised as a SalI fragment, and ligated into SalI-digested, calf alkaline phosphatase-treated M13mp9 (commercially available), generating the M13 vector MGX68 (FIG. 3). The MGX68 single-stranded template and a 36-base oligonucleotide were then used to delete the 15-base pair sequence containing the glu-ala-glu-ala-trp codons, which separate the alpha-factor spacer, lys-arg, from mature At-III. The deleted vector was designated MGX69 (FIG. 3) and the expected sequence was confirmed by DNA sequence analysis.

Figure 4:
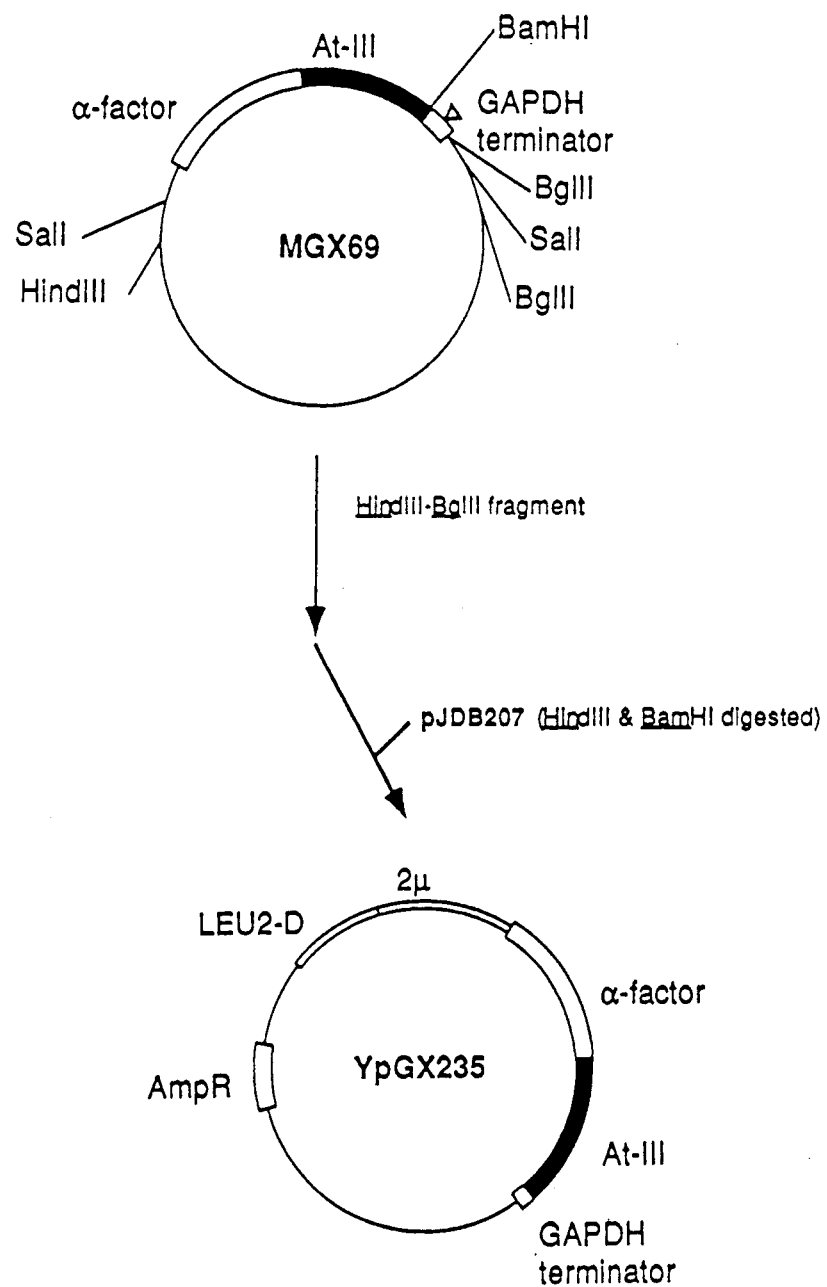
FIG. 4 is a flow chart showing the construction of expression vector YpGX235.

The alpha-factor/At-III DNA sequence from MGX69 was then used to construct expression vector, YpGX235. To generate YpGX235, the alpha-factor-/At-III sequence was excised from MGX69 as a HindIII-BglII fragment which was ligated to HindIII-BamHI digested pJDB207 (FIG. 4) (BglII and BamHI generate the same 5' single-stranded ends).

Transformation of S. cerevisiae with the Alpha-Factor/
At-III Expression Vector

The alpha-factor/At-III expression vector YpGX235 was introduced by transformation into several yeast host strains. These included both MAT (Mating Type) a and MAT alpha strains. However, efficient transformation was observed only when MAT a hosts were transformed. (Although when MAT-alpha cells were transformed with YpGX235, small colonies were observed microscopically, they stopped growing before visible colonies were seen.) The most obvious explanation for the inability to isolate viable YpGX235 transformants of MAT alpha cells is that the AT-III expression levels from YpGX235 are high enough to be lethal to the cells. In MAT a hosts, it is expected that alpha-factor-directed expression would be considerably lower than that in MAT alpha hosts. Previous studies have shown that alpha-factor-directed invertase expression, based on a 2 micron plasmid of medium copy number, is 60-70 fold higher in MAT alpha cells than in MAT a cells. Emr et al., Proc. Natl. Acad. Sci. USA 80: 7080-7084(1983).

The inability to stably transform MAT alpha hosts with YpGX235 indicated that high-level constitutive expression of At-III in S. cerevisiae may not be compatible with cell growth and division. To alleviate this problem it was necessary to tightly regulate the expression of At-III in S. cerevisiae, so that high-level expression, occured after the logarithmic growth phase.

EXPERIMENTAL RESULTS AND METHODS
FOR THE EXPRESSION OF BIOLOGICALLY
ACTIVE AT-III IN S. CEREVISIAE

Figure 5:
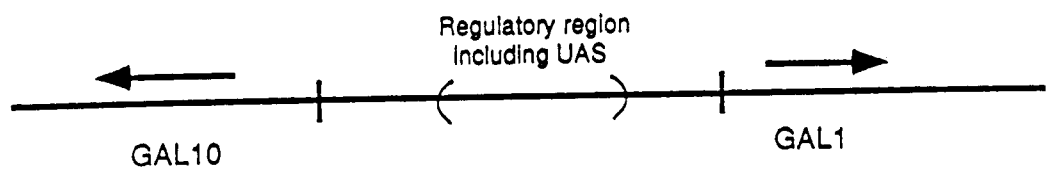
FIG. 5 shows the organization of the GAL1-10 genes in *S. cerevisiae*.

Construction of a Galactose-Regulated Gene Encoding
Alpha-Factor Prepro-Lys-Arg-At-III The GAL1-10 regulatory region. In order to tightly regulate expression of the gene encoding alpha-factor prepro-lys-arg-At-III, the upstream activation site (UAS) of the GAL1-10 regulatory region was positioned 5' of the alpha-factor transcription initiation site (TIS) present in vector MGX69. The GAL1 and GAL10 genes are located within 560 base pairs of each other on chromosome II of Saccharomyces, but are transcribed from opposite strands (FIG. 5). Sequences within the 560-base pair intergene region include the GAL1 and GAL10 TIS and UAS sequences. The UAS specifically determines the regulated expression of the GAL1 and GAL10 genes in response to galactose.

Oshima, "Regulatory Circuit for Gene Expression: The Metabolism of Galactose and Phosphate," in, J. Strathern et al., eds., *The Molecular Biology of the Yeast Saccharomyces: Life Cycle and Inheritance*, Cold Spring Harbor Laboratory, Publisher, N.Y., pp. 159-180 (1982), describes the regulation of galactose metabolic genes in yeast. The current hypothesis is that the UAS sequences preceding each gene bind a positive regulatory protein encoded by the GAL4 gene. A negative regulatory protein encoded by the GAL80 gene is also involved in the control of galactose gene expression. In the absence of galactose, the GAL4 and GAL80 proteins form a complex that prevents binding of the GAL4 protein to the UAS sequences, and therefore no active transcription of the GAL genes occurs. In the presence of galactose, the GAL4-GAL80 protein complex dissociates, releasing the GAL4 protein which can then bind to the GAL UAS sequences to stimulate active transcription of the GAL1 and the GAL10 genes. To test this hypothesis, the effects of perturbations of the system, such as inactivation of the GAL80 protein by mutation or boosting the level of GAL4 protein by recombinant DNA techniques, have been examined. Johnston et al., *Proc. Natl. Acad. Sci. USA* 79:6971-6975 (1982). As expected excess active GAL4 protein leads to constitutive expression of the galactose genes. However, the genes are still subject to glucose repression, and growth of yeast cells in media containing high levels of glucose overrides "constitutive" expression of the galactose genes.

The GAL1-10 UAS region previously has been utilized successfully to regulate expression of another yeast gene, CYC1, with galactose. Guarante et al., *Proc. Natl. Acad. Sci. USA 79:* 7410-7414 1982). In addition, results have been published that more specifically define the GAL1-10 UAS sequences. Giniger et al., *Cell* 40: 767-774 1985).

Oligonucleotide-directed mutagenesis of the GAL1-10 regulatory region

Figure 6:
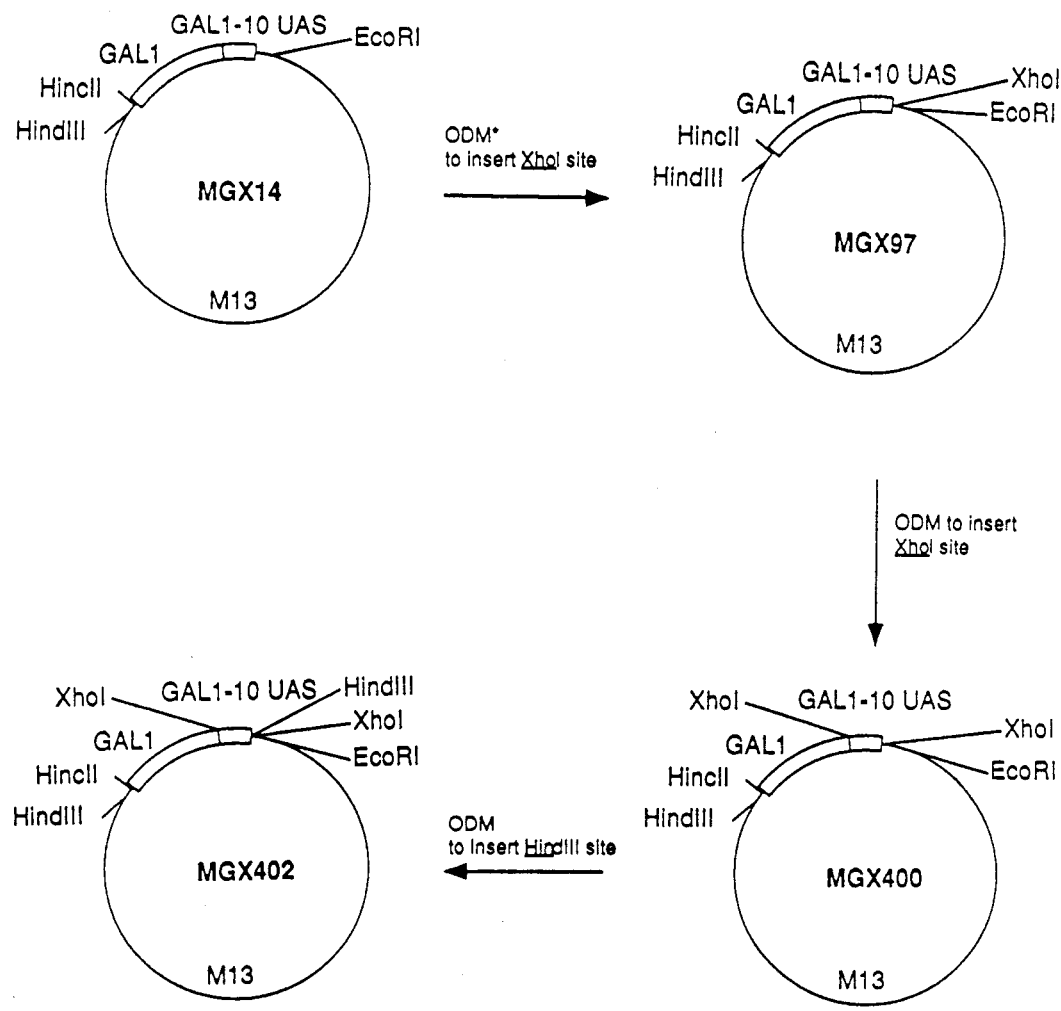
FIG. 6 shows the addition of HindIII and XhoI sites to the GAL1-10 regulatory region.
Figure 7:
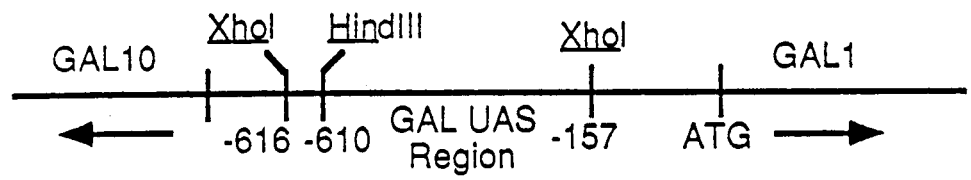
FIG. 7 is a restriction map showing restriction sites in the GAL1-10 regulatory region created by oligonucleotide-directed mutagenesis.

An M13 vector carrying the GAL1-10 regulatory region, MGX14 (FIG. 6), was assembled by ligating a HincII-EcoRI GAL1-10 fragment to HincII- and EcoRI-digested M13mp9. The HincII and EcoRI sites in MGX14 are located in the 201st and 45th codons of the GAL1 and GAL10 genes, respectively. In describing the location of restriction endonuclease recognition sites added to the GAL1-10 regulatory region, the A in the ATG translation initiation codon of GAL1 is defined as +1 and the preceding base as -1. Using MGX14 as the initial template, three restriction sites were added sequentially to the GAL1-10 regulatory region by oligonucleotide-directed mutagenesis (FIG. 6). First, a 38-base oligonucleotide was utilized as a primer to insert four bases and create an XhoI site at position -616. The vector with this mutation, MGX97, was then mutagenized using a 41-base oligonucleotide as a primer to create a second XhoI site at position -157. Finally, this vector, MGX400, served as the template for a third mutagenesis, in which five base pairs were inserted using a 36-base oligonucleotide primer to create a HindIII restriction site at position -610. The final vector, MGX402, thus contains two new XhoI sites and one new HindIII site. The GAL UAS region can be conveniently excised from MGX401 either as an XhoI-XhoI or XhoI-HindIII restriction fragment. A summary of these new restrictions sites and their location in the GAL1-10 region is depicted in FIG. 7.

Oligonucleotide-directed mutagenesis of the alphafactor regulatory region

Figure 8:
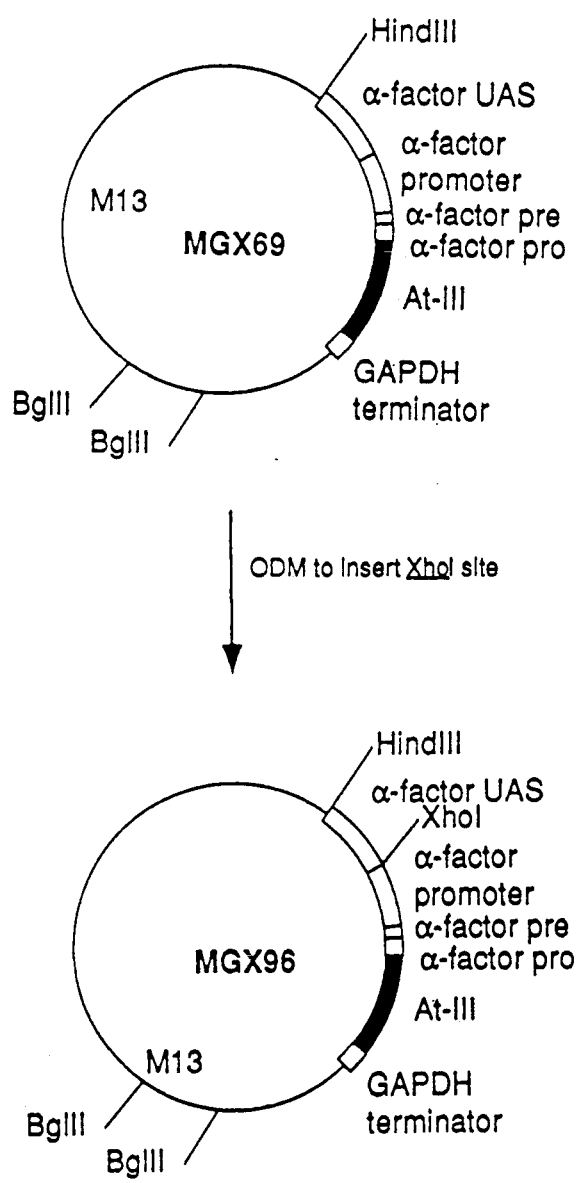
FIG. 8 is a flow chart showing the addition of a XhoI site to the alpha-factor regulatory region.

The regulatory region of the alpha-factor gene (MF-alpha-1) is not as well defined as is the GAL1-10 regulatory region. Nevertheless, the present inventors were able to predict the approximate locations of the alpha-factor UAS and TIS. The mating type-regulated alpha-factor prepro-lys-arg-At-III gene had previously been cloned into M13. That vector, MGX69, was used as a template for the insertion of a XhoI restriction site at position -158 relative to the ATG start codon (FIG. 8). This new XhoI site permitted the alpha-factor UAS to be conveniently separated from the alpha-factor TIS.

Figure 9:
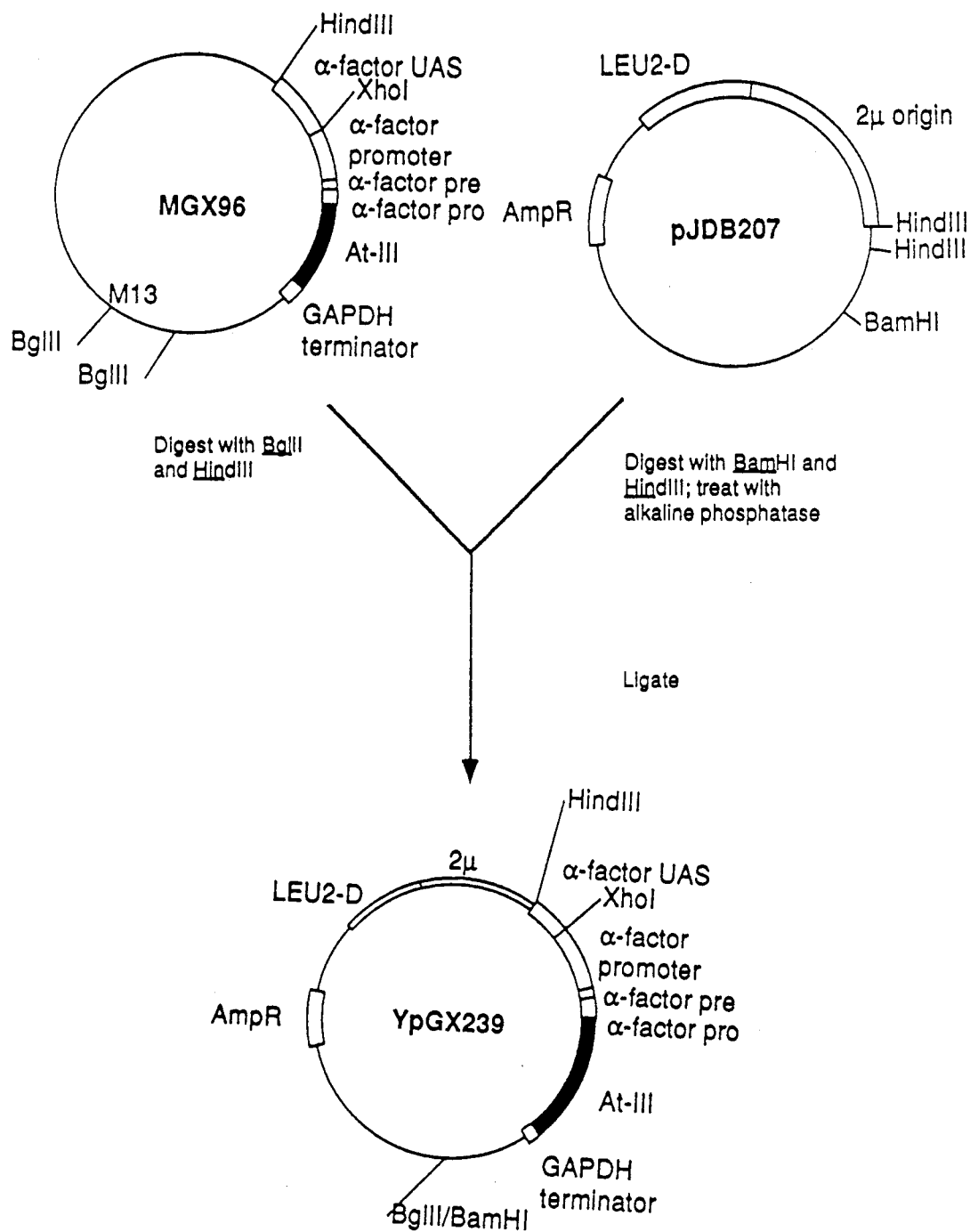
FIG. 9 is a flow chart showing the assembly of a yeast-*E. coli* shuttle vector including the alpha-factor prepro-Lys-Arg-At-III gene.
Figure 10:
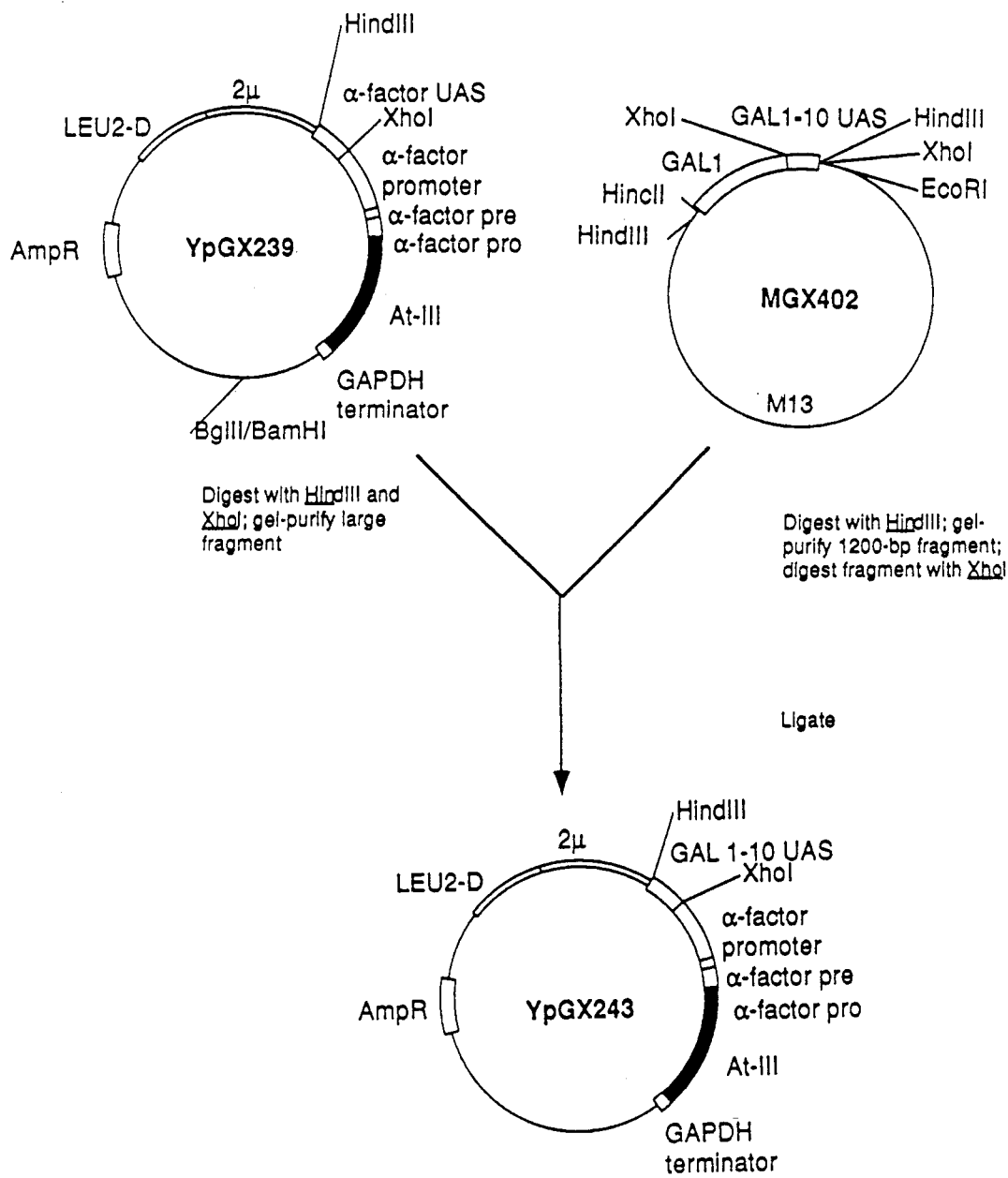
FIG. 10 is a flow chart showing the insertion of a GAL upstream activation site adjacent to the alpha-factor prepro-Lys-Arg-At-III gene.

Construction of the galactose-regulated alpha-factor prepro-lys-arg-At-III gene in a yeast-E. coli shuttle vector The GAL1-10 UAS and alpha-factor prepro-lys-argAT-III gene were then joined in yeast-*E. coli* shuttle vector pJDB207. The vector includes the yeast 2 micron replication origin and the LEU2-d gene which allows selection for high-copy number in Saccharomyces. The first step in this construction involved introduction of the alpha-factor prepro-lys-arg-At-III gene from MGX96 into pJDB207 (FIG. 9). This was accomplished by excising the alpha-factor pre-pro-lys-arg-At-III gene as a HindIII-BqlII restriction fragment from MGX96 and ligating with pJDB207, which had been cleaved with HindIII and BamHI and treated with calf alkaline phosphatase. The resulting plasmid vector, YpGX239, is identical to the previously constructed vector YpGX235 with the exception of the added XhoI site in the alpha-factor regulatory region. To replace the alpha-factor UAS in YpGX239 with the GAL1-10 UAS, the steps outlined in FIG. 10 were performed. The GAL1-10 UAS was excised from MGX402 on a 1,200-bp HindIII fragment which was then gel-purified and cleaved with XhoI. YpGX239 was digested with HindIII and XhoI and the large vector fragment was gel-purified. The HindIII-XhoI fragments were then ligated to generate YpGX243.

Production of alpha-Factor Prepro-Lys-Arq-At-III in Yeast Cells Transformed with YpGX243

To test for galactose-regulated expression of alpha-factor prepro-lys-arg-At-III, various *S. cerevisiae* strains were transformed with vector YpGX243. Whereas great difficulty was encountered in transforming MAT alpha hosts with YpGX235, YpGX243 transformed MAT alpha and MAT a hosts equally well. The transformed yeast cells were grown in a medium containing 1% yeast extract, 1% Bacto-Peptone, 2% glucose (YPD) and then induced for At-III production by shifting to a similar medium (YPGal) containing 2% galactose in place of the glucose. Production of AT-III was measured by radioimmunoassay (RIA). The results for strain G20(YpGX243) showed that at 16 hours only 0.05% of the total soluble protein was At-III cross-reacting material (CRM). The results did however, indicate that expression of the alpha-factor prepro-lysarg-At-III gene is galactose-regulated. However, RIA determination under-estimates total At-III in the cell because the majority of the At-III produced is insoluble, and thus is not detected by the RIA.

An interesting result which suggested that At-III production in G20(YpGX243) was limited by a genetic factor was that, unlike the non-transformed host, this strain grew poorly on YPGal medium. Because the AtIII production was quite low and not likely to limit cell growth, it seemed probable that the chromosomal galactose metabolic genes were being inefficiently expressed. The present inventors reasoned that the problem could be a very low level of GAL4 protein in relation to the number of GAL1-10 UAS sequences. It is believed that the GAL4 protein (a positive regulator) binds specifically to GAL1-10 UAS, promoting transcription of the galactose metabolic genes by RNA polymerase. Because yeast cells transformed with YpGX243 have a hundred-fold more GAL UAS sequences in comparison with the non-transformed host cell, the GAL4 levels might not be sufficient to efficiently promote expression of both the chromosomal GAL genes and the plasmid-encoded galactose-regulated At-III gene.

Methods to Increase the GAL4 Gene Copy Number

To compensate for the possibility that the poor growth of G20(YpGX243) on YPGal medium was due to insufficient GAL4 product, the copy number of the GAL4 gene in yeast cells transformed with YpGX243 was increased. The GAL4 gene has been cloned on plasmid pSJ3 (Johnston et al., Proc. Natl. Acad. Sci. USA 79: 6971-6975 (1982) a yeast-E. coli shuttle vector.

Figure 11:
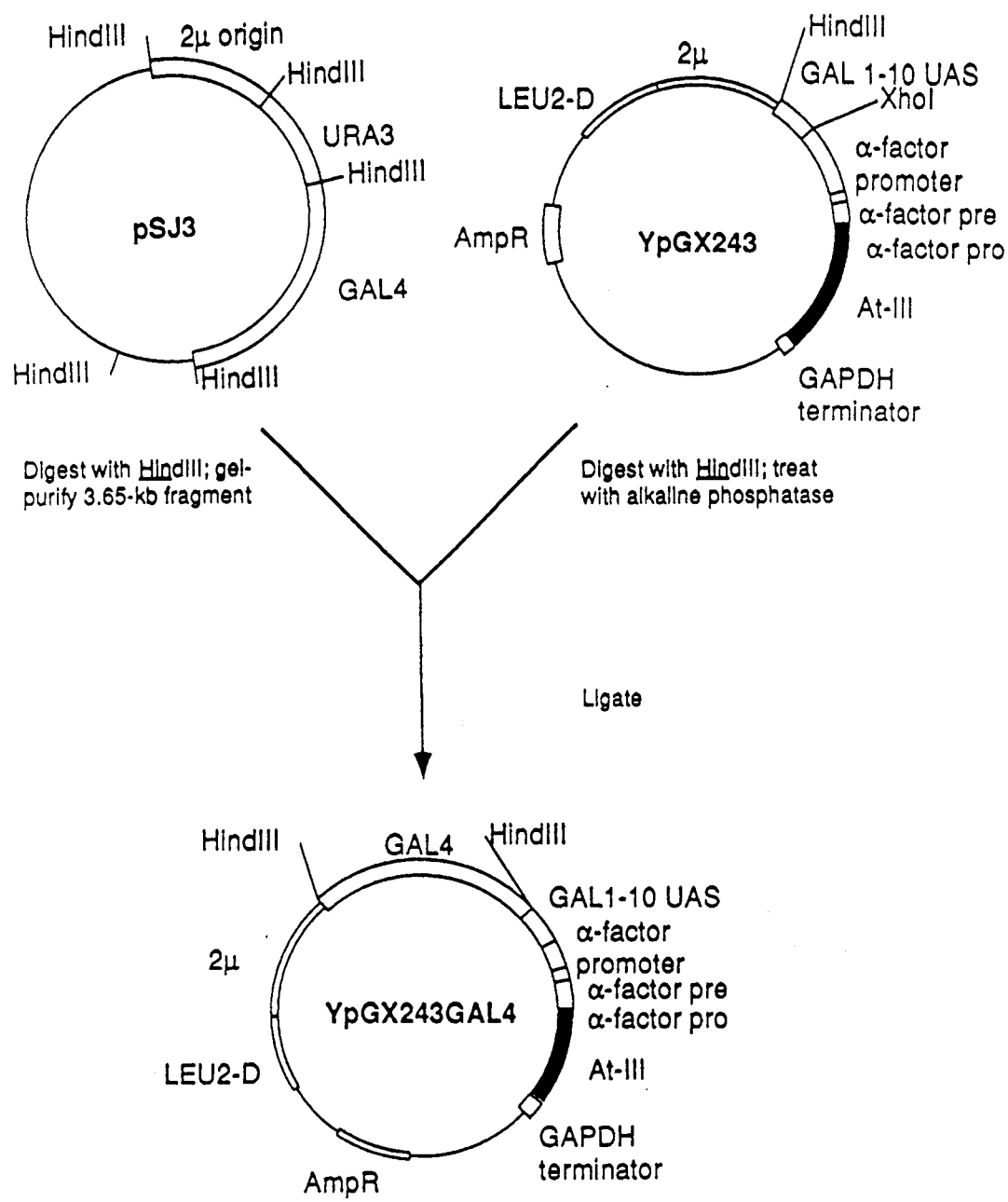
FIG. 11 is a flow chart showing the insertion of the GAL4 gene into the plasmid YpGX243.

The approach was to directly insert the GAL4 gene into plasmid YpGX243 (FIG. 11). The GAL4 gene from pSJ3 was excised as a HindIII fragment and ligated to the unique HindIII site of plasmid YpGX243 The resulting vector, YpGX243GAL4, was used to transform S. cerevisiae strain G20. These strains then had the same number of copies of the GAL4 gene and the galactose-regulated alpha-factor prepro-lys-arg-At-III gene. In a second approach, yeast strain 422, which carries chromosomal mutations both in the LEU2 and URA3 genes, was transformed with both plasmids (YpGX243 and pSJ3). This approach also yielded enhanced GAL4 product and increased AT-III expression. Another suitable host strain for use in this approach is SHY1 (ATCC Accession No. 44769).

Figure 12:
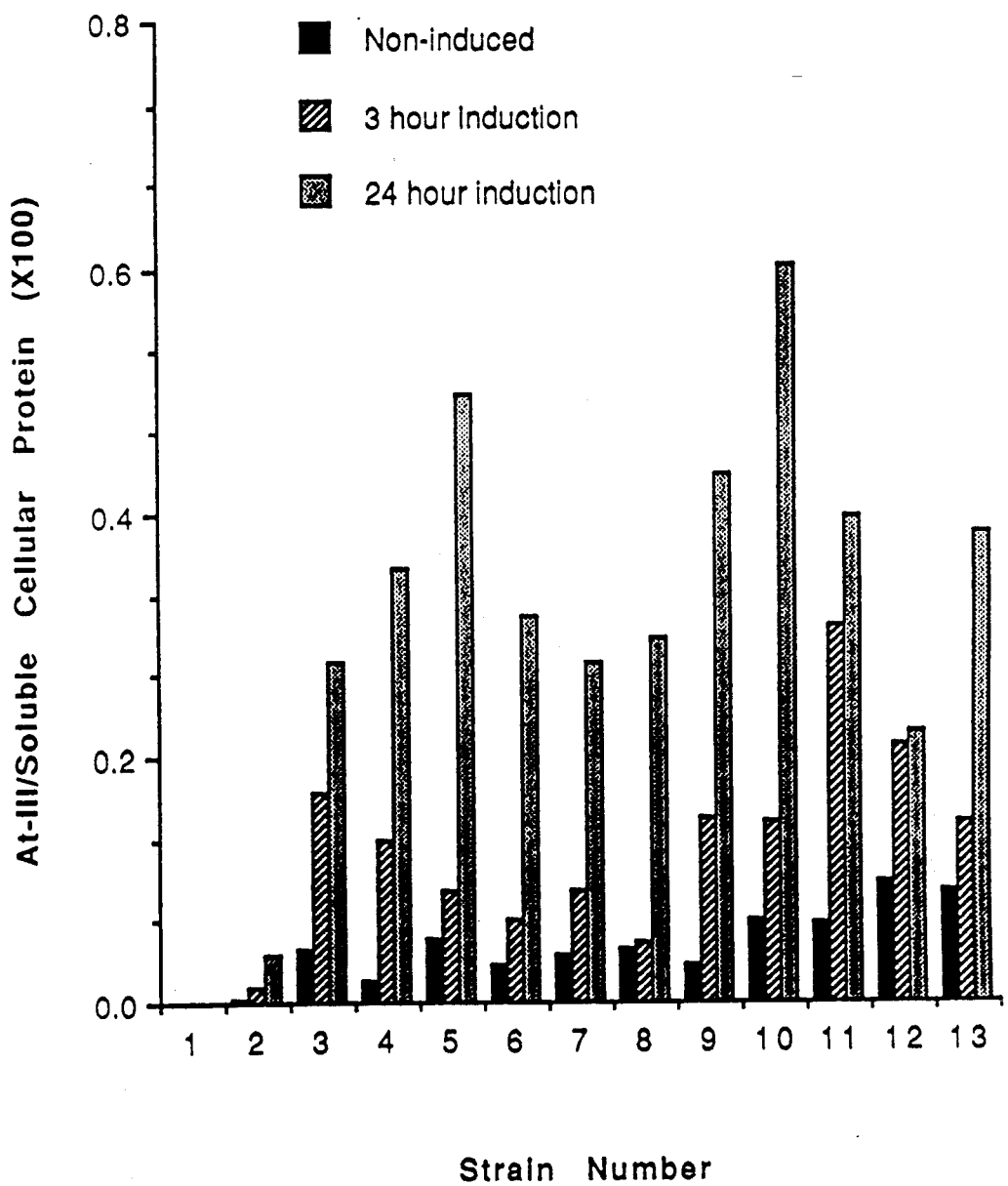
FIG. 12 shows galactose-regulated expression of At-III. For each strain, the first bar represents a non-galactose-induced culture, the second a three-hour galactose induction, and the third a 16-hour galactose induction. The host strain genotypes are: G10 (MATa leu2-3 leu2-112), 422 (MATa leu2-3 leu2-112 ura3 his3), and D5 (MATαleu2-3 leu2-112 sec18). At-III protein is measured by RIA.

Cultures of the transformed cells were induced with galactose and At-III CRM levels were again monitored by RIA at 0, 3 and 16 hours after induction (FIG. 12). The data for strains G20(YpGX243GAL4) and G20(YpGX243) clearly demonstrate that At-III expression is more efficient when additional copies of GAL4 are present. It is clear that increasing the copy number of the GAL4 gene does increase the level of At-III CRM produced.

Generation of Galactose- or Alpha-Factor-Regulated Genes Encoding Alpha-Factor Pre-At-III To delete the alpha-factor pro sequence from MGX69 by oligonucleotide-directed mutagenesis, a 36-base oligonucleotide was used as the primer. The mutagenesis deleted 195 base pairs, including the alphafactor pro sequence and the lys-arg spacer residues, to yield vector MGX92 (FIG. 13). In preparation for inserting the GAL1-10 UAS, an XhoI site was inserted into the alpha-factor regulatory region of MGX92 by oligonucleotide-directed mutagenesis, generating vector MGX403 (FIG. 13).

An expression vector that includes the alphafactor pre-At-III gene was assembled by excising the alpha-factor pre-At-III gene from MGX92 as a HindIII-BglII fragment and ligating it with pJDB207 which had been cleaved with BamHI and HindIII and treated with calf alkaline phosphatase (FIG. 14). The resulting vector, YpGX241, is identical to YpGX235 with the exception that the alpha-factor pro-lys-arg sequence is deleted.

A galactose-regulated version of this gene was generated in two steps (FIGS. 15 amd 16). First, MGX403 was cleaved with HindIII and BglII and ligated with BamHI- and HindIII-digested, calf alkaline phosphatase-treated pJDB207 to generate YpGX245 (FIG. 15). The GAL1-10 UAS was then inserted into YpGX245 by digesting with HindIII and XhoI, isolating the large vector fragment, and ligating this fragment with the XhoI-HindIII GAL1-10 UAS fragment from MGX402 (FIG. 16). The newly assembled vector was designated YpGX246.

The GAL4 gene was then added to YpGX246 by isolating it from pSJ3 as a 3.65-kb HindIII fragment and ligating that fragment with HindIII-digested, calf alkaline phosphatase-treated YpGX246 (FIG. 17). The newly assembled vector was designated YpGX-246GAL4.

Deletion of the MF-alpha-1 Pre Coding Sequence

The 57-base pair alpha-factor pre sequence was deleted from MGX92 using a 36-base oligonucleotide primer (FIG. 18). The resulting vector carrying the desired met-AT-III gene was designated MGX404. Again, in preparation for insertion of the GAL1-10 UAS, a XhoI site was inserted at position −158 relative to the start of the MF-alpha-1 gene of MGX404 by oligonucleotide-directed mutagenesis, generating MGX408.

Although galactose regulation of the alpha-factor/At-III gene led to improved levels of At-III protein expression (10–30 mg per liter of culture), the inventors positioned other signal encoding sequences at the 5' end of the gene (directly 5' to the mature At-III coding sequence) to determine whether other sequences in the translation initiation region might improve translation efficiency of mRNA encoded by these vectors. The signals utilized included those encoded by the yeast PHO5 and SUC2 genes, and the natural At-III signal.

Construction of expression/secretion vectors encoding the PHO5 signal linked to mature At-III The PHO5 signal is comprised of 17 amino acids (including the methionine initiation codon). Since insertion of the entire PHO5 signal-coding sequence requires 48 nucleotides, we performed two consecutive mutageneses to complete this construction. Starting with single-stranded template DNA from vector MGX408 (FIG. 19), a mutagenesis was performed using a 54 base oligonucleotide to insert the coding sequence for the 8 C-terminal amino acids of the PHO5 signal. The mutagenized vector was screened with the mutagenic oligonucleotide by hybridization and putative positive clones were analyzed by DNA sequencing. A vector carrying the desired sequence was designated MGX425 (FIG. 19). Single-stranded template prepared from this vector was mutagenized using a 54 base oligonucleotide to insert the N-terminal portion of the PHO5 signal-coding sequence. Positive clones were again screened by hybridization and the correct sequence was confirmed by DNA sequencing. The new vector (MGX428) contains the PHO5 signal (FIG. 19). The presence of the entire PHO5 signal was confirmed by DNA sequence analysis.

The DNA fragment encoding the PHO5 signal fused to mature At-III was excised from double-stranded MGX428 DNA using HindIII and BglII restriction endonucleases (FIG. 20). The fragment was then inserted into the yeast-E. coli shuttle vector YpGX243 which had been digested with HindIII and BamHI and treated with calf alkaline phosphatase (CAP). Ligation of the isolated At-III fragment from MGX428 with the prepared plasmid YpGX243 generated vector YpGX261 (FIG. 20). This vector contains all of the elements necessary to produce At-III in yeast using the MF-alpha-1 promoter.

Because tightly regulated expression of At-III is necessary to achieve high expression levels in yeast, the MF-alpha-1 UAS was replaced with the UAS derived from the GAL1-10 regulatory region. First, the MF-alpha-1 UAS was excised from YpGX261 as a HindIII-XhoI restriction fragment (FIG. 21) and the plasmid was treated with calf alkaline phosphatase. The large vector fragment was then gel-purified. The GAL1-10 UAS was isolated from plasmid YpGX243 by digesting that vector with restriction endonucleases HindIII and XhoI and gel purifying the small fragment. Ligation of the purified GAL1-10 UAS with the enzymatically prepared YpGX243 plasmid fragment generated YpGX262 (FIG. 21). This plasmid is identical to YpGX263 except that the MF-alpha-1 UAS is replaced by the GAL1-10 UAS.

To achieve efficient expression using the galactose regulatory system, it is necessary to provide extra copies of the gene encoding the GAL4 protein, a positive regulator of this system. The GAL4 gene was excised from plasmid YpGX243GAL4 as a HindIII restriction fragment (FIG. 22) and the gel-purified 3.65 kb fragment was ligated with HindIII-linearized, calf alkaline phosphatase-treated YpGX262. The new plasmid, YpGX262GAL4, was utilized to express the galatose-regulated PHO5 signal-At-III sequence in yeast.

Construction of expression/secretion vectors encoding the two additional forms of At-III The expression/secretion vectors encoding the other signal sequences were generated in a very similar manner to that described for the PHO5 signal. The main difference was the number of rounds of oligonucleotide-directed mutagenesis used to create the desired signal sequence.

Construction of the expression/secretion vectors containing the invertase (SUC2) signal fused to the coding sequence for mature At-III is described in FIGS. 23 through 26. Because the SUC2 signal is only 19 amino acids long, two rounds of mutagenesis were sufficient to insert this sequence. The final set of expression/secretion vectors, those containing the At-III signal sequence, was constructed as described in FIGS. 27 through 30. Three rounds of mutagenesis were required to insert this signal sequence.

The level of soluble At-III protein produced by strain D8 transformed with the newly constructed expression vectors is shown in Table I. Soluble At-III levels for strains that produce PHO5 signal-At-III and natural pre-At-III are quite high, measuring 121 mg/l and 17.4 mg/l, respectively.

To measure the level of insoluble At-III protein produced by PHO5 signal-At-III-containing strains, the Western blots of insoluble and soluble At-III protein were compared. This indicated that insoluble At-III protein accumulates at about 1 g/1 in shake-flask cultures of these strains. Such ultrahigh expression could not have been predicted from previous results.

EXAMPLE II

Assembly of an Expression Vector Encoding PHO5 Signal-At-III

A cDNA gene encoding antithrombin-III protein is prepared as described by Bock et al. (U.S. Pat. No. 4,157,294) and is cloned into an E. coli plasmid such as pTA2.

The AT-III cDNA coding sequence is excised from pTA2 as an EcoRI-PstI fragment. A limited PstI digest permits isolation of molecules which have not been digested within the At-III coding sequence.

Double-stranded phage M13mp18 DNA is digested with restriction endonucleases EcoRI and PstI, and the large vector fragment is gel purified. This DNA molecule is ligated with the EcoRI-PstI At-III cDNA and, following transformation of E. coli M13, plaques containing the recombinant DNA molecules are identified by restriction digest analysis. To place a restriction endonuclease restriction site immediately following the TAA translation stop codon, oligonucleotide directed mutagenesis, (Zoller et al., Ann. Rev. Genetics 19:423-462 (1985)), is performed. In this case a restriction endonuclease recognition site for BamHI is inserted immediately after the TAA codon. A suitable oligonucleotide to prime this mutagenesis is:

5'GCAAAGAATAAGAACATTGGATCCT-
TACTTAACACAAGG

The mutagenized molecules containing the new BamHI site are identified by digesting double-stranded DNA with BamHI and determining which molecules are linearized. The presence and proper positioning of the BamHI site is confirmed by DNA sequence analysis. (Sanger, Science 214:1205-1210 (1981)). This M13 vector is called M13At-2.

To place a SmaI restriction endonuclease site at the start of the mature At-III coding region, double-stranded M13At-2 DNA is digested with EcoRI and SacII, and the large vector fragment is gel purified. The 5' coding region of At-III and a SmaI site are then added by ligating the gel purified M13At-2 DNA with two oligonucleotides which have been annealed. Suitable oligonucleotides for this purpose are:

```
A 5'  AATTCCCGGGCACGGTTCTCCGGTTGACATCTGCACCGCGAAACCGC
B 3'       GGGCCCGTGCCAAGAGGCCAACTGTAGACGTGGCGCTTTGG
```

Following transformation of E. coli, phage molecules carrying the inserted oligonucleotides are identified by hybridization and the sequence is confirmed by DNA sequence analysis. The vector so prepared is M13-At-3.

The At-III cDNA molecule is excised from M13At-3 using the SmaI and BamHI restriction sites and reintroduced by ligation into M13mp18 which has been digested with SmaI and BamHI. The new M13 vector is M13At-4. Double-stranded M13At-4 is digested with SmaI. The DNA is then digested with HindIII and the At-III-containing fragment is gel purified.

The yeast upstream activation site (UAS) and transcription initiation site (TIS), and PHO5 signal encoding region are removed from vector YpGX265GAL4 (Deposited as ATCC #67233) (FIG. 31) by digesting with HindIII and EcoRV and the fragment is gel purified. This fragment is ligated with the previously prepared M13At-4 DNA and HindIII linearized M13mp18 DNA in a three-way ligation. Following transformation of E. coli vector molecules carrying the At-III sequence in phase with yeast signal sequence are identified by restriction digestion.

To create a molecule in which the PHO5 signal encoding sequence is linked to the cDNA encoding mature At-III without extraneous nucleotides, an oligonucleotide directed mutagenesis is performed to delete those bases. A suitable oligonucleotide to prime this mutagenesis is:

5' GTCAACCGGAGAACCGTGAGCGTTGG-
CCAAAGAAGC

Mutant clones can then be identified by hybridization with oligonucleotide used for mutagenesis (which is now labeled with $^{32}$P) and the sequence is confirmed by DNA sequence analysis. The vector is called M13At-5. The yeast UAS, TIS and signal encoding sequences and the At-III gene are then from double-stranded M13At-5 by digesting with HindIII and BamHI.

YpGX265GAL4 is digested with HindIII to excise the GAL4 gene, which is then gel purified and saved. The plasmid fragment is then digested with BamHI and the large vector fragment is gel purified. This fragment is then ligated with the purified M13-At-5 BamHI-HindIII fragment. The desired plasmid is identified by restriction endonuclease analysis and is called YpGX262.

YpGX262 is linearized with enzyme HindIII and treated with calf alkaline phosphate. The HindIII GAL4 fragment is ligated with the HindIII-linearized calf alkaline phosphatase-treated YpGX262. Following transformation of E. coli, recombinant DNA molecules carrying the GAL4 gene are identified. The vector is called YpGX262GAL4.

Deletion of the PHO5 Signal Encoding Sequence

M13mp9 (commercially available) is digested with enzymes BamHI and HindIII and gel purified. YpGX262 is digested with HindIII and BamHI and the fragment carrying the UAS, TIS, signal and At-III is gel purified. These two DNA fragments are ligated and E. coli is transformed. The desired vector, MGX428', is identified by restriction analysis of double-stranded DNA. Single-stranded template MGX428' DNA is prepared and oligonucleotide directed mutagenesis is performed to delete the PHO5 signal encoding sequence. A suitable oligonucleotide to prime this mutagenesis is:

5' GTCAACC-
GGAGAACCGTGTCTTTTGGTCGTT-
TATATTGTG

Mutant clones are identified by probing with an oligonucleotide of this sequence, which recognizes the boundaries on either end of the PHO5 signal encoding sequence. Successful completion of the mutagenesis is confirmed by DNA sequence analysis. The new vector is MGX408'. This vector carries the coding sequence for methionine-At-III.

Assembly of an Expression Vector Encoding SUC2 Signal-At-III

Template DNA is prepared from MGX408' in preparation for oligonucleotide directed mutagenesis. The SUC2 signal sequence is inserted at the 5' end of the At-III gene in two consecutive insertion mutageneses. An appropriate oligonucleotide for the first step has the sequence

5' AACCGGAGAACCGTGCAAAAGGAAAAGGAAGGCTTGCAAAAGCA
TTCTTTTGGTCGT

This oligonucleotide is used as the primer for oligonucleotide directed mutagenesis to insert the C terminus of the SUC2 signal encoding sequence. The mutagenic oligonucleotide is then labeled with $^{32}$P and used as a probe to screen M13 plaques for the presence of the insertion. The sequence is confirmed by DNA sequence analysis. The desired mutant clone is called MGX419'.

Single-stranded MGX419' template DNA is prepared and used in a second round of mutagenesis in which the remaining coding sequence for the SUC2 is inserted. The oligonucleotide used to prime this mutagenesis is

5' AACCGGAGAACCGTGTGCAGATATTTTGGCTGCAAAACCAGCCAAAA
GGAAAAGGAA

As in previous examples the mutagenic oligonucleotide can then be labeled with 32P and used to detect mutant clones by hybridization screening. Molecules which are positive in this hybridization screen are then analyzed by DNA sequence analysis to confirm the successful mutagenesis. The new vector, MGX420', carries the entire coding sequence for the SUC2 signal linked to the AT-III coding sequence.

The UAS, TIS, signal coding sequence, and At-III coding sequence are excised from double-stranded MGX420' DNA with restriction endonuclease HindIII and BamHI and purified by gel electrophoresis.

YpGX262 is digested with enzymes BamHI and HindIII and the large vector fragment is gel purified. A ligation is performed with these two DNA fragments and E. coli is then transformed. The E. coli transformants are then screened by restriction digest analysis for insertion of the DNA fragment from MGX420'. The desired plasmid is called YpGX254.

YpGX254 is digested with HindIII and then treated with calf alkaline phosphatase. The HindIII fragment from YpGX265GAL4 carrying the GAL4 gene is then inserted into this vector by ligation and E. coli cells are transformed. The desired plasmid is identified by restriction digest analysis and is called YpGX254GAL4.

Assembly of an Expression Vector Encoding Pre-At-III

Template DNA is prepared from MGX408' for use in oligonucleotide directed mutagenesis. The At-III signal sequence as determined by Bock et al. (U.S. Pat. No. 4,517,294) is inserted at the 5' end of the At-III gene in three consecutive insertion mutageneses. An appropriate oligonucleotide for the first step has the sequence.

```
5' GTCAACCGGAGAACCGTGACAGGTCACGCAGTCCCAGAA
   GCCAATGAGCATTTTGGTCGTTTATATTGT
```

This oligonucleotide is used as the primer for oligonucleotide directed mutagenesis to insert the C terminus of the At-III signal encoding sequence. The mutagenic oligonucleotide is then labeled with $^{32}$P and used as a probe to screen M13 plaques for the presence of the insertion. The sequence is confirmed by DNA sequence analysis. The desired mutant clone is called MGX429'.

Single-stranded MGX429' template DNA is prepared and used in a second round of mutagenesis in which the coding sequence for the middle of the At-III signal is inserted. The oligonucleotide used to prime this mutagenesis is

```
5' CCCAGAAGCCAATGAGCAGCAAGGACAAAAGATAAA
   CCTTCCTTTTTCCCATTTTGGTCGTTTATATTGTG
```

As in previous steps, the mutagenic oligonucleotide can then be labeled with $^{32}$P and used to detect mutant clones by hybridization screening. Molecules which are positive in this hybridization screen are then analyzed by DNA sequence analysis to confirm the successful mutagenesis. The new vector, MGX430', carries approximately two-thirds of the At-III signal coding sequence linked to the mature At-III coding sequence.

Template DNA is prepared from MGX430' and used in a mutagenesis with an oligonucleotide which provides the remaining coding sequence for the At-III signal N-terminus. The oligonucleotide has the sequence:

```
5' AAACCTTCCTTTTTCCAGAGGTTACAGTTCCTATCACATTGGAA
   TACATTTTGGTCGTTTATATTGTG
```

Following mutagenesis with this oligonucleotide, again a hybridization screen with $^{32}$P-labeled mutagenic oligonucleotide reveals single-stranded DNA molecules from the M13 plaques containing the desired sequence. The presence of the coding region for the entire AT-III signal is confirmed by DNA sequence analysis. The new vector is called MGX431'.

The promoter, signal coding sequence, and mature At-III coding sequence are excised from double-stranded ed MGX431' DNA with restriction endonucleases, HindIII and Bam HI and purified by gel electrophoresis.

YpGX262 is digested with enzymes BamHI and HindIII and the large vector fragment is gel purified. A ligation is performed with the DNA fragments and E. coli is then transformed. The E. coli transformants are then screened by restriction digest analysis for insertion of the DNA fragment from MGX431'. The desired plasmid is called YpGX264.

YpGX264 is digested with HindIII and then treated with calf alkaline phosphatase. The HindIII fragment from YpGX265GAL4 carrying the GAL4 gene is then inserted into this vector by ligation and E. coli cells are transformed. The desired plasmid is identified by restriction digest analysis and is called YpGX264GAL4.

Assembly of an Expression Vector Encoding Methionine-Proline-At-III al. (U.S. Pat. No.

According to Daum et al. (U.S. Pat. No. 4,543,329), it should be possible to produce methionine-proline-At-III in a microorganism and then process that molecule in vitro to generate mature At-III. To assemble a vector for production of that molecule the following procedure is followed.

Template DNA is prepared from MGX408' in preparation for oligonucleotide directed mutagenesis. A proline codon is inserted between the methionine initiation codon and the mature At-III coding sequence. An appropriate oligonucleotide for this step has the sequence

```
5' CGGAGAACCGTGTG-
   GCATTCTTTTGGTCG
```

The mutagenic oligonucleotide is then labeled with $^{32}$P and used as a probe to screen M13 plaques for the presence of the insertion. The sequence is confirmed by DNA sequence analysis. The desired mutant clone is called MGX423'.

The promoter, signal coding sequence, and At-III coding sequence are excised from double-stranded MGX423' DNA with restriction endonuclease HindIII and BamHI and purified by gel electrophoresis. YpGX262 is digested with enzymes BamHI and HindIII and the large vector fragment is gel purified.

A ligation is performed with these two DNA fragments and E. coli is then transformed. The E. coli transformants are then screened by restriction digest analysis for insertion of the DNA fragment from MGX423'. The desired plasmid YpGX256.

YpGX256 is digested with HindIII and then treated with calf alkaline phosphatase. The HindIII fragment from YpGX265GAL4 carrying the GAL4 gene is then inserted into this vector by ligation and E. coli cells are transformed. The desired plasmid is identified by restriction digest analysis and is called YpGX256GAL4.

Tranformation of Yeast and Induction of Foreign Gene Expression

The method of Hinnen et al., Proc. Natl. Acad. Sci. USA 75:1929–1933 (1978) is used to transform appropriate yeast strains such as D8. Appropriate strains for these studies are ones which have nuclear mutations in the S. cerevisiae LEU2 gene. ATCC strain #44769, for example, is appropriate for this purpose. The transformed yeast strains are maintained on a medium composed of 0.7% yeast nitrogen base, 10% glucose (YNBD10) plus appropriate nutritional supplements, if required.

To grow the transformed cells for production of the foreign protein these cells are transferred to a medium composed of yeast extract (1%), peptone (2%), glucose (1%), galactose (1%) and grown for 1-2 days at 30° C. with shaking. Alternatively the cells can be grown to high density using only glucose as the carbon source, and as the glucose is exhausted expression of the foreign protein will commence.

A third method used to induce expression of the protein product is as follows. The cells were inoculated into culture medium composed of yeast nitrogen base (0.7%) and 2% glucose. These cells were grown for approximately 16 hours at 30° C. with shaking.

TABLE I

Production of soluble At-III Protein by Various Strains

| Strain | At-III | Regulation | Soluble AT-III (mg/l)[1] |
|---|---|---|---|
| D8(YpGX243GAL4) | α-factor prepro-lys-arg-At-III | GAL | 2.73 |
| D8(YpGX254GAL4) | SUC2 signal-At-III | GAL | 3.60 |
| D8(YpGX255) | met-pro-At-III | α-factor | 2.12 |
| D8(YpGX256GAL4) | met-pro-At-III | GAL | 5.50 |
| D8(YpGX262GAL4) | PHO5 signal-At-III | GAL | 121.0 |
| D8(YpGX264GAL4) | At-III signal-At-III | GAL | 17.4 |

[1]Soluble At-III protein was determined by radioimmunoassay. The protein level is expressed as milligrams per liter of yeast culture. Western blot analysis of insoluble and soluble At-III produced by these strains indicated that about 10% of the At-III was soluble.

The cells were then pelleted by centrifugation and resuspended to the original volume in medium composed of yeast extract 1%, peptone (2%) and glucose (2%). the cells were grown for approximately 24 hours at 30° C. with shaking. These cells were then pelleted by centrifugation and resuspended to the original volume in medium composed of yeast extract (1%), peptone (2%) and galactose (2%) and grown for approximately 24 hours at 30° C. with shaking. The cells were pelleted by centrifugation and then broken by vortexing with glass beads in a buffer composed of 25mM Tris, 125mM EDTA, pH 8.4. The soluble and insoluble cellular proteins were separated by centrifugation and the amount of antithrombin III protein in the soluble fraction was measured by radioimmunoassay. The results of these assays for strain D8 transformed with the At-III expression vectors listed are presented in Table I.

In addition, comparable amounts of yeast soluble and insoluble protein from the transformed strains were compared by Western blot analysis. These Western blots indicated that only about 10% of the antithrombin III produced by these strains is in the soluble fraction and therefore the total amount of antithrombin III accumulating in the cells after induction is about 10 fold more than the value indicated in the radioimmunoassay.

To confirm that very high levels of antithrombin III protein were remaining associated with the insoluble yeast cellular protein, this protein fraction from strain DB(YpGX262GAL4) was examined by SDS-polyacrylamide gel electrophoresis according to the method of Lemmlae, Nature 227:680-685(1970). Samples from cells grown in YPD (no galactose induction) or YPGal (galactose induced) were compared. As can be seen in FIG. 32, following staining of the gel with Coomassie brilliant blue, a prominent band of antithrombin III protein appeared only in the induced sample. This protein routinely composed 25-50% of the total yeast insoluble protein observed by this method.

What is claimed is:

1. A DNA sequence comprising
   (a) a hybrid yeast promoter comprising the functional segment of the DNA sequence encoding the upstream activation site of a gene selected from the group consisting of GAL1, GAL7 and GAL10, operably linked to the functional segment of the transcription initiation site of MF-α-1;
   (b) the functional segment of a PHO5 signal sequence substantially comprising preferred yeast codons, wherein said signal sequence is operably linked to said hybrid yeast promoter;
   (c) the functional segment of the DNA sequence comprising a Saccharomyces GAPDH transcription terminator, wherein restriction sites are situated between said signal sequence and said transcription terminator for insertion of heterologous genes linked in phase to said signal sequence and said transcription terminator;
   (d) the functional segment of the Saccharomyces 2μ circle replication origin; and
   (e) the functional segment of the yeast LEU2-d selectable marker.

2. The DNA sequence of claim 1, further comprising, inserted in phase between the signal sequence and transcription terminator, the functional segment of a DNA sequence encoding a heterologous target peptide.

3. The DNA sequence of claim s 1 or 2, wherein said upstream activation site of step (a) is that of GAL1.

4. The DNA sequence of claims 1 or 2, wherein said upstream activation site of step (a) is that of GAL7.

5. The DNA sequence of claims 1 or 2, wherein said upstream activation site of step (a) is that of GAL10.

6. The DNA sequence of claim 1 or 2 wherein said signal sequence comprises:

ATGTTCAAATCTGTTGTTTACT-
CTATTTTGGCTGCTTCTTTGG-
CCAACGCT.

7. The DNA sequence of claims 1 or 2, wherein said yeast is Saccharomyces.

8. The DNA sequence of claim 7, wherein said Saccharomyces is S. cerevisiae.

9. The DNA sequence of claims 1 or 2, wherein said transcription initiation site comprises bases −158 to −1 of said MF-α-1, as shown in FIG. 33.

10. The DNA sequence of claims 1 or 2, wherein said upstream activation site comprises bases −610 to −157 as shown in FIG. 34.

11. The DNA sequence of claims 1 or 2, wherein said transcription terminator of step (c) comprises:

GGATCCCGGGTTTTTTATAGCTTTAT-
GACTTAGTTTCAATTATATACTATT-
TAATGACATTTTCAG.

12. The DNA sequence of claims 1 or 2, wherein said replication origin of step (d) is derived from said plasmid pJDB207.

13. The DNA sequence of claims 1 or 2, wherein said selectable marker of step (e) is derived from plasmid pJDB207.

14. A DNA expression vector comprising the DNA sequence of claim 2.

15. The DNA expression vector of claim 14, wherein said vector is a plasmid.

16. The DNA expression vector of claim 14, wherein said vector is an E. coli/Saccharomyces shuttle vector.

17. A DNA expression system comprising the vector of claims 14, 15 or 16 and a source of the peptide encoded by the DNA sequence of the GAL4 structural gene.

18. The DNA expression system of claim 17, wherein said source of said peptide encoded by the DNA sequence of the GAL4 structural gene comprises a second expression vector comprising a yeast expressible DNA sequence of the GAL4 structural gene.

19. The DNA expression system of claim 17, wherein said source of said peptide encoded by the DNA sequence of the GAL4 structural gene is present in said DNA expression vector.

20. A LEU2-d deficient Saccharomyces host transformed with the DNA expression vector of claims 14, 15 or 16.

21. A LEU-2 deficient Saccharomyces host transformed with the DNA expression system of claim 17.

22. The host of claims 20 wherein said Saccharomyces is S. cerevisiae.

23. Yeast strain designated YpGX265GAL4, Accession No. ATCC 67233.

24. A method for producing a heterologous target peptide in a LEU2-d deficient Saccharomyces host, comprising transforming said host with the DNA expression vector of claims 14, 15 or 16, culturing the thus transformed host in a suitable culture medium, inducing expression of said target peptide by increasing the galactose concentration of said medium, and recovering said target peptide.

25. A method for producing a heterologous target peptide in a LEU2-d deficient Saccharomyces host, comprising transforming said host with the DNA expression system of claim 17, culturing the thus transformed host in a suitable culture medium, inducing expression of said target peptide by increasing the galactose concentration of said medium, and recovering said target peptide.

* * * * *